United States Patent
Brooks et al.

(10) Patent No.: US 11,028,099 B2
(45) Date of Patent: Jun. 8, 2021

(54) NRF2 ACTIVATORS

(71) Applicant: GLAXOSMITHKLINE INTELLECTUAL PROPERTY DEVELOPMENT LIMITED, Middlesex (GB)

(72) Inventors: Carl A. Brooks, King of Prussia, PA (US); Jay M. Matthews, King of Prussia, PA (US)

(73) Assignee: GLAXOSMITHKLINE INTELLECTUAL PROPERTY DEVELOPMENT LIMITED, Brentford (GB)

( * ) Notice: Subject to any disclaimer, the term of this patent is extended or adjusted under 35 U.S.C. 154(b) by 0 days.

(21) Appl. No.: 16/469,203

(22) PCT Filed: Dec. 11, 2017

(86) PCT No.: PCT/IB2017/057804
§ 371 (c)(1),
(2) Date: Jun. 13, 2019

(87) PCT Pub. No.: WO2018/109646
PCT Pub. Date: Jun. 21, 2018

(65) Prior Publication Data
US 2020/0031846 A1 Jan. 30, 2020

Related U.S. Application Data

(60) Provisional application No. 62/434,745, filed on Dec. 15, 2016.

(51) Int. Cl.
C07D 498/04 (2006.01)
A61K 9/00 (2006.01)
C07C 215/12 (2006.01)

(52) U.S. Cl.
CPC ............ C07D 498/04 (2013.01); A61K 9/007 (2013.01); A61K 9/0019 (2013.01); A61K 9/0053 (2013.01); C07C 215/12 (2013.01)

(58) Field of Classification Search
CPC .. C07D 267/02; C07D 267/12; C07D 249/04; C07D 498/04
See application file for complete search history.

(56) References Cited

U.S. PATENT DOCUMENTS 10,604,509 B2 * 3/2020 Kerns .................. C07D 401/14
2019/0330238 A1 * 10/2019 Callahan .............. C07D 417/14

FOREIGN PATENT DOCUMENTS

| WO | WO 2015/092713 A1 | 6/2015 |
| WO | WO 2016/202253 A1 | 12/2016 |
| WO | WO 2016/203400 A1 | 12/2016 |
| WO | WO 2016/203401 A1 | 12/2016 |
| WO | WO 2018/104766 A1 | 6/2018 |

* cited by examiner

*Primary Examiner* — Theodore R. Howell
*Assistant Examiner* — George W Kosturko
(74) *Attorney, Agent, or Firm* — Nora L. Stein; Fang Qian; Duke M. Fitch

(57) ABSTRACT

The present invention relates to a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid (I), or a pharmaceutically acceptable salt thereof, in particular, the meglumine salt thereof, a pharmaceutical composition containing the compound and its use as an NRF2 activator.

(I)

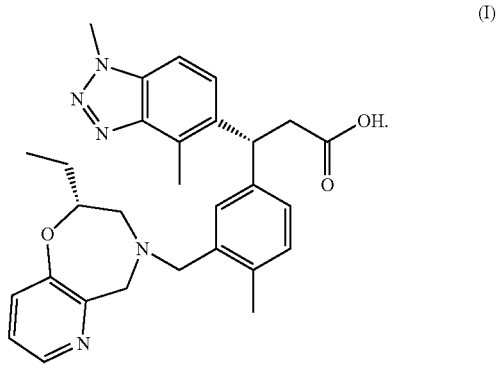

2 Claims, 1 Drawing Sheet

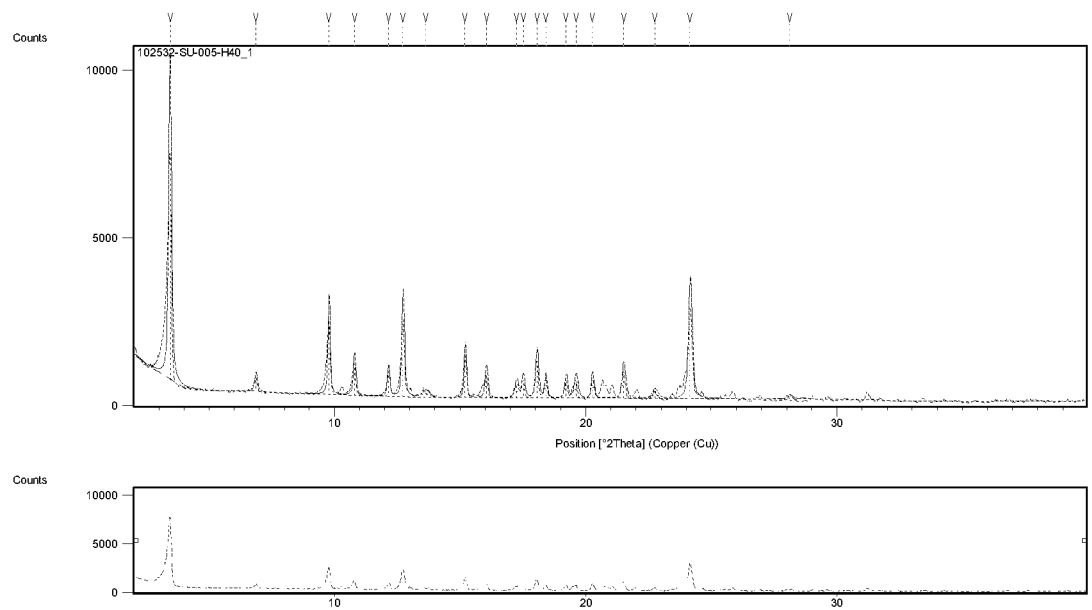

NRF2 ACTIVATORS

FIELD OF THE INVENTION

The present invention relates to the compound (R)-3-(1, 4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt thereof, in particular, the meglumine salt thereof, a pharmaceutical composition containing the compound and its use as an NRF2 activator.

BACKGROUND OF THE INVENTION

NRF2 (NF-E2 related factor 2) is a member of the cap-n-collar family of transcription factors containing a characteristic basic-leucine zipper motif. Under basal conditions, NRF2 levels are tightly controlled by the cytosolic actin-bound repressor, KEAP1 (Kelch-like ECH associating protein 1), which binds to NRF2 and targets it for ubiquitylation and proteasomal degradation via the Cul3-based E3-ubiquitin ligase complex. Under conditions of oxidative stress, DJ1 (PARK7) is activated and stabilizes NRF2 protein by preventing NRF2 from interacting with KEAP1. Also, modification of reactive cysteines on KEAP1 can cause a conformational change in KEAP1 that alters NRF2 binding and promotes NRF2 stabilization. Thus, the levels of NRF2 in the cell are usually kept low in normal conditions but the system is designed to respond quickly to environmental stress by increasing NRF2 levels and thus downstream NRF2 activity.

Inappropriately low NRF2 activity in the face of on-going oxidative stress appears to be a pathological mechanism underlying chronic obstructive pulmonary disease (COPD). Yamada, K., et al. BMC Pulmonary Medicine, 2016, 16: 27. This may be a result of an altered equilibrium between NRF2 activators with both inappropriate lack of positive activators such as DJ1, and overabundance of negative activators such as Keap1 and Bach1. Therefore, restoration of NRF2 activity in the lungs of COPD patients should result in repair of the imbalance and mitigation of deleterious processes such as apoptosis of structural cells (including alveolar epithelial and endothelial cells) and inflammation. The results of these effects would be enhanced cytoprotection, preservation of lung structure, and structural repair in the COPD lung, thus slowing disease progression. Therefore, NRF2 activators may treat COPD (Boutten, A., et al. 2011. Trends Mol. Med. 17:363-371) and other respiratory diseases, including asthma, Acute Lung Injury (ALI) (Cho, H. Y., and Kleeberger, S. R., 2015, Arch Toxicol. 89:1931-1957; Zhao, H. et al., 2017, Am J Physiol Lung Clee Mol Physiol 312:L155-L162, first published Nov. 18, 2016; doi:10.1152/ajplung.00449.2016), Acute Respiratory Distress Syndrome (ARDS) and pulmonary fibrosis (Cho, H. Y., and Kleeberger, S. R. 2010. Toxicol. Appl. Pharmacol. 244:43-56).

The therapeutic potential of an NRF2 activator is exemplified in pulmonary macrophages from COPD patients where NRF2 pathway appears maladaptive. These cells have impaired bacterial phagocytosis compared with similar cells from control patients, and this effect is reversed by the addition of NRF2 activators in vitro. Therefore, in addition to the effects mentioned above, restoration of appropriate NRF2 activity could also rescue COPD exacerbations by reducing lung infection.

This is demonstrated by the NRF2 activator, Sulforaphane, which increases the expression of Macrophage Receptor with Collagenous structure (MARCO) by COPD macrophages and alveolar macrophages from cigarette smoke-exposed mice, thereby improving in these cells bacterial phagocytosis (Pseudomonas aeruginosa, non-typable Haemophilus influenzae) and bacterial clearance both ex vivo and in vivo. (Harvey, C. J., et al. 2011. Sci. Transl. Med. 3:78ra32).

The therapeutic potential of targeting NRF2 in the lung is not limited to COPD. Rather, targeting the NRF2 pathway could provide treatments for other human lung and respiratory diseases that exhibit oxidative stress components such as chronic asthma and acute asthma, lung disease secondary to environmental exposures including but not limited to ozone, diesel exhaust and occupational exposures, fibrosis, acute lung infection (e.g., viral (Noah, T. L. et al. 2014. PLoS ONE 9(6): e98671), bacterial or fungal), chronic lung infection, al antitrypsin disease, ALI, ARDS and cystic fibrosis (C F, Chen, J. et al. 2008. PLoS One. 2008; 3(10): e3367).

A therapy that targets the NRF2 pathway also has many potential uses outside the lung and respiratory system. Many of the diseases for which an NRF2 activator may be useful are autoimmune diseases (psoriasis, IBD, MS), suggesting that an NRF2 activator may be useful in autoimmune diseases in general.

In the clinic, a drug targeting the NRF2 pathway (bardoxolone methyl) has shown efficacy in diabetic patients with diabetic nephropathy/chronic kidney disease (CKD) (Aleksunes, L. M., et al. 2010. J. Pharmacol. Exp. Ther. 335:2-12), though phase III trials with this drug in patients with the most severe stage of CKD were terminated. Furthermore, there is evidence to suspect that such a therapy would be effective in sepsis-induced acute kidney injury, other acute kidney injury (AKI) (Shelton, L. M., et al. 2013. Kidney International. June 19. doi: 10.1038/ki.2013.248), and kidney disease or malfunction seen during kidney transplantation.

In the cardiac area, bardoxolone methyl is currently under investigation in patients 30 with Pulmonary Arterial Hypertension and so a drug targeting NRF2 by other mechanisms may also be useful in this disease area. Oxidative stress is increased in the diseased myocardium, resulting in accumulation of reactive oxygen species (ROS) which impairs cardiac function [Circ (1987) 76(2); 458-468] and increases susceptibility to arrhythmia [J of Mol & Cell Cardio (1991) 23(8); 899-918] by a direct toxic effect of increased necrosis and apoptosis [Circ Res (2000) 87(12); 1172-1179]. In a mouse model of pressure overload (TAC), NRF2 gene and protein expression is increased during the early stage of cardiac adaptive hypertrophy, but decreased in the later stage of maladaptive cardiac remodeling associated with systolic dysfunction [Arterioscler Thromb Vasc Biol (2009) 29(11); 1843-5 1850; PLOS ONE (2012) 7(9); e44899]. In addition, NRF2 activation has been shown to suppress myocardial oxidative stress as well as cardiac apoptosis, fibrosis, hypertrophy, and dysfunction in mouse models of pressure overload [Arterioscler Thromb Vasc Biol (2009) 29(11); J of Mol & Cell Cardio (2014) 72; 305-315; and 1843-1850; PLOS ONE (2012) 7(9); e44899]. NRF2 activation has also been shown to protect against cardiac I/R injury in mice 10 [Circ Res (2009) 105(4); 365-374; J of Mol & Cell Cardio (2010) 49(4); 576-586] and reduce myocardial oxidative damage following cardiac I/R injury in rat. Therefore, a drug targeting NRF2 by other mechanisms may be useful in a variety of cardiovascular diseases including but not limited to atherosclerosis, hypertension, and heart failure (Oxidative Medicine and Cellular Longevity Volume 2013 (2013), Article ID 104308, 10 pages), acute coronary 15 syndrome, myocardial infarction, myocardial repair, cardiac remodeling, cardiac arrhythmias, heart failure with preserved ejection fraction, heart failure with reduced ejection fraction and diabetic cardiomyopathy.

A drug activating the NRF2 pathway could also be useful for treatment of several neurodegenerative diseases including Parkinson's disease (PD), Alzheimer's disease (AD), amyotrophic lateral sclerosis (ALS) (Brain Res. 2012 Mar. 29; 1446:109-18. 2011.12.064. Epub 2012 Jan. 12) and multiple sclerosis (MS). Multiple in vivo models have shown that NRF2 KO mice are more sensitive to neurotoxic insults than their wild-type counterparts. Treatment of rats with the NRF2 activator tert-butylhydroquinone (tBHQ) reduced cortical damage in rats in a cerebral ischemia-reperfusion model, and cortical glutathione levels were increased in NRF2 wild-type but not KO mice after administration of tBHQ (Shih, A. Y., et al. 2005. J. Neurosci. 25: 10321-10335). Tecfidera™ (dimethyl fumarate), which activates NRF2 among other targets, is approved in the U.S. to treat relapsing-remitting multiple sclerosis (MS). Activation of NRF2 may also help treat cases of Friedreich's Ataxia, where increased sensitivity to oxidative stress and impaired NRF2 activation has been reported (Paupe V., et al, 2009. PLoS One; 4(1):e4253. Omaveloxolone (RTA-408) is also in clinical trials for Friedreich's Ataxia.

There is preclinical evidence of the specific protective role of the NRF2 pathway in models of inflammatory bowel disease (IBD, Crohn's Disease and Ulcerative Colitis) and/ or colon cancer (Khor, T. O., et al 2008. Cancer Prev. Res. (Phila) 1:187-191).

Age-related macular degeneration (AMD) is a common cause of vision loss in people over the age of 50. Cigarette smoking is a major risk factor for the development of non-neovascular (dry) AMD and perhaps also neovascular (wet) AMD. Findings in vitro and in preclinical species support the notion that the NRF2 pathway is involved in the anti-oxidant response of retinal epithelial cells and modulation of inflammation in pre-clinical models of eye injury (Schimel, et al. 2011. Am. J. Pathol. 178:2032-2043). Fuchs Endothelial Corneal Dystrophy (FECD) is a progressive, blinding disease characterized by corneal endothelial cells apoptosis. It is a disease of aging and increased oxidative stress related to low levels of NRF2 expression and/or function (Bitar, M. S., et al. 2012. Invest Ophthalmol. Vis. Sci. Aug. 24, 2012 vol. 53 no. 9 5806-5813). In addition, an NRF2 activator may be useful in uveitis or other inflammatory eye conditions.

Non-alcoholic steatohepatitis (NASH) is a disease of fat deposition, inflammation, and damage in the liver that occurs in patients who drink little or no alcohol. In preclinical models, development of NASH is greatly accelerated in KO mice lacking NRF2 when challenged with a methionine- and choline-deficient diet (Chowdhry S., et al. 2010. Free Rad. Biol. & Med. 48:357-371). Administration of the NRF2 activators oltipraz and NK-252 in rats on a choline-deficient L-amino acid-defined diet significantly attenuated progression of histologic abnormalities, especially hepatic fibrosis (Shimozono R. et al. 2012. Molecular Pharmacology. 84:62-70). Other liver diseases that may be amenable to NRF2 modulation are toxin-induced liver disease (e.g., acetaminophen-induced hepatic disease), viral hepatitis, and cirrhosis (Oxidative Medicine and Cellular Longevity Volume 2013 (2013), Article ID 763257, 9 page).

Recent studies have also begun to elucidate the role of ROS in skin diseases such as psoriasis. A study in psoriasis patients showed an increase in serum malondialdehyde and nitric oxide end products and a decrease in erythrocyte-superoxide dismutase activity, catalase activity, and total antioxidant status that correlated in each case with disease severity index (Dipali P. K., et al. Indian J Clin Biochem. 2010 October; 25(4): 388-392). Also, an NRF2 activator may be useful in treating the dermatitis/topical effects of radiation (Schafer, M. et al. 2010. Genes & Devl. 24:1045-1058), and the immunosuppression due to radiation exposure (Kim, J. H. et al., J. Clin. Invest. 2014 Feb. 3; 124(2): 730-41).

There are also data suggesting that an NRF2 activator may be beneficial in preeclampsia, a disease that occurs in 2-5% of pregnancies and involves hypertension and proteinuria (Annals of Anatomy—Anatomischer Anzeiger Volume 196, Issue 5, September 2014, Pages 268-277).

Hutchinson-Gilford progeria syndrome (Progeria) is a rare, invariably fatal premature aging disorder. The disease is caused by constitutive production of progerin, a mutant form of the nuclear architectural protein lamin A, leading, through unknown mechanisms, to diverse morphological, epigenetic, and genomic damage and to mesenchymal stem cell (MSC) attrition in vivo. There are findings that identify repression of the NRF2-mediated antioxidative response as a key contributor to the premature aging phenotype (Kubben, N. et al., 2016, Cell 165, 1361-1374).

Cardiorenal syndrome is a complicated and bidirectional interrelationship between the heart and kidneys. Naringenin (NG) is a naturally occurring flavonoid possessing various biological and pharmacological properties. NG increased the expression of NRF2. Inhibition of NRF2 markedly suppressed NG-induced increase of GCLc expression in Ang II-treated cardiac fibroblasts (Liu et al., Journal of Surgical Research, Jun. 15, 2016 (203) 416-423).

Preclinical data has shown that compounds with NRF2 activating activity are better at reversing high altitude-induced damage than compounds without NRF2 activity, using animal and cellular models of Acute Mountain Sickness (Lisk C. et al, 2013, Free Radic Biol Med. October 2013; 63: 264-273.)

There are also data suggesting that an NRF2 activator may be beneficial in Sickle cell disease (SCD) which is an inherited disorder caused by a point mutation in the β-globin gene, leading to the production of abnormally shaped red blood cells. Sickle cells are prone to hemolysis and thereby release free heme into plasma, causing oxidative stress and inflammation that in turn result in damage to multiple organs (Keleku-Lukwete, N. et al., 2015, PNAS, vol. 112, no. 39, 12169-12174; Belcher, J. D. et al., Antioxidants & Redox Signaling, 2016, DOI: 10.1089/ars.2015.6571; Owusu-Anash, A. et al., Front. Med. 2015, 9(1): 46-56).

NRF2 activators have been disclosed in WO 2015/092713, published Jun. 25, 2015, and in copending patent applications PCT/IB2016/053544, filed Jun. 15, 2016; PCT/IB2016/053545, filed Jun. 15, 2016; PCT/US2016/057387; filed Dec. 6, 2016; and PCT/CN2016/085806, filed Jun. 15, 2015.

In particular, a mixture of stereoisomers at the beta-stereocenter which contains 50% of a compound of the invention ((R)-3-(1,4-dimethyl-1H-benzo[d][1,2,3]triazol-5-yl)-3-(3-(((R)-2-ethyl-2,3-dihydropyrido[2,3-f][1,4] oxazepin-4(5H)-yl)methyl)-4-methylphenyl)propanoic acid), is disclosed as Example 79 (3-(1,4-Dimethyl-1H-benzo[d][1,2,3]triazol-5-yl)-3-(3-(((R)-2-ethyl-2,3-dihydro-pyrido[2,3-t][1,4]oxazepin-4(5H)-yl)methyl)-4-methylphe-nyl)propanoic acid) in PCT/CN2016/085806. The S-beta-stereocenter isomer be (S)-3-(1,4-dimethyl-1H-benzo[d][1, 2,3]triazol-5-yl)-3-(3-(((R)-2-ethyl-2,3-dihydropyrido[2,3- f][1,4]oxazepin-4(5H)-yl)methyl)-4-methylphenyl)propanoic acid, is disclosed as Example 258 in PCT/CN2016/085806.

It will be understood that the compound of the invention is an inhibitor/antagonist of KEAP1 complex which regulates NRF2 concentrations. The inhibition of the KEAP1 protein leads to the activation/agonism of NRF2. It has now been discovered that the compound of of the invention is particularly useful for activating NRF2.

SUMMARY OF THE INVENTION

In one aspect, this invention provides for a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt thereof.

In a second aspect, this invention provides for a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a meglumine salt thereof.

In a further aspect, this invention provides for a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoicacid, (−)-1-Deoxy-1-(methylamino)-D-glucitol salt. It will be understood that this is the meglumine salt of (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoicacid.

In another aspect, this invention provides for the use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid or a pharmaceutically acceptable salt thereof, as an NRF2 activator. It will be understood that this invention provides for the use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a meglumine salt thereof, as an NRF2 activator.

In yet another aspect, the invention provides a pharmaceutical composition comprising (R)-3-(1,4-dimethyl-1H-benzo[d][1,2,3]triazol-5-yl)-3-(3-(((R)-2-ethyl-2,3-dihydropyrido[2,3-][1,4]oxazepin-4(5H)-yl)methyl)-4-methylphenyl)propanoic acid, or a pharmaceutically acceptable salt thereof, and a pharmaceutically acceptable excipient. Particularly, this invention is directed to a pharmaceutical composition for the treatment of an NRF2-regulated disease or disorder (including the respiratory and non-respiratory disorders disclosed herein), wherein the composition comprises a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid or a pharmaceutically acceptable salt thereof, and a pharmaceutically acceptable excipient. It will be understood that a pharmaceutical composition of the invention comprises (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a meglumine salt thereof, and a pharmaceutically acceptable excipient.

In a further aspect, this invention provides for a method of treating respiratory and non-respiratory disorders, including COPD, asthma, ALI, ARDS, fibrosis, chronic asthma, acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, acute kidney injury (AKI), kidney disease or malfunction seen during kidney transplantation, Pulmonary Arterial Hypertension, hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy atherosclerosis, Parkinson's disease (PD), Alzheimer's disease (AD), Friedreich's Ataxia (FA), amyotrophic lateral sclerosis (ALS), multiple sclerosis (MS), inflammatory bowel disease, colon cancer, neovascular (dry) AMD and neovascular (wet) AMD, eye injury, Fuchs Endothelial Corneal Dystrophy (FECD), uveitis or other inflammatory eye conditions, Non-alcoholic Steatohepatitis (NASH), toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, high altitude sickness, Sickle cell disease (SCD), Progeria and Cardiorenal Syndrome (CRS), which comprises administering to a patient, particularly a human, in need thereof, a therapeutically effective amount of a compound which is (R)-3-(1,4-dimethyl-1H-benzo[d][1,2,3]triazol-5-yl)-3-(3-(((R)-2-ethyl-2,3-dihydropyrido[2,3-t][1,4]oxazepin-4(5H)-yl)methyl)-4-methylphenyl)propanoic acid, or a pharmaceutically acceptable salt thereof. It will be understood that this invention provides for a method of treating the respiratory and non-respiratory disorders disclosed herein which comprises administering to a patient, particularly a human, in need thereof, a therapeutically effective amount of a compound which is (R)-3-(1,4-dimethyl-1H-benzo[d][1,2,3]triazol-5-yl)-3-(3-(((R)-2-ethyl-2,3-dihydropyrido[2,3-t][1,4]oxazepin-4(5H)-yl)methyl)-4-methylphenyl)propanoic acid, or a meglumine salt thereof.

In still yet another aspect, this invention provides for the use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl) propanoic acid or a pharmaceutically acceptable salt thereof, for the treatment of the respiratory and non-respiratory disorders disclosed herein. It will be understood that this invention provides for the use of a compound which is (R)-3-(1,4-dimethyl-1H-benzo[d][1,2,3]triazol-5-yl)-3-(3-(((R)-2-ethyl-2,3-dihydropyrido[2,3-t][1,4]oxazepin-4(5H)-yl)methyl)-4-methylphenyl)propanoic acid, or a meglumine salt thereof, for the treatment of the respiratory and non-respiratory disorders disclosed herein.

In a further aspect, this invention relates to use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid or a pharmaceutically acceptable salt thereof, in the manufacture of a medicament for the treatment of respiratory and non-respiratory disorders disclosed herein. It will be understood that this invention provides for the use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a meglumine salt thereof, in the manufacture of a medicament for the treatment of respiratory and non-respiratory disorders disclosed herein.

In another aspect, this invention relates to a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid or a pharmaceutically acceptable salt thereof, for use in the treatment of the respiratory and non-respiratory disorders disclosed herein. It will be understood that this invention provides for a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a meglumine salt thereof, for use in the treatment of the respiratory and non-respiratory disorders disclosed herein.

In a further aspect, this invention provides for a method of treating hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy, SCD, Progeria and CRS, which comprises administering to a patient, in particular, a human in need thereof, a therapeutically effective amount of a compound which is (R)-3-(1,4-dimethyl-1H-benzo[d][1,2,3]triazol-5-yl)-3-(3-(((R)-2-ethyl-2,3-dihydropyrido[2,3-t][1,4]oxazepin-4(5H)-yl)methyl)-4-methylphenyl)propanoic acid, or a pharmaceutically acceptable salt thereof. It will be understood that this invention provides for a method of treating the diseases mentioned herein which comprises administering to a patient, particularly a human, in need thereof, a therapeutically effective amount of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a meglumine salt thereof.

In yet another aspect, this invention provides for the use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt thereof, for the treatment of hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy, SCD, Progeria and CRS. It will be understood that this invention provides for the use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a meglumine salt thereof for the treatment of the diseases mentioned herein.

In a further aspect, this invention relates to use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt thereof, in the manufacture of a medicament for the treatment of hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy, SCD, Progeria and CRS. It will be understood that this invention provides for the use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a meglumine salt thereof, in the manufacture of a medicament for the treatment of the diseases mentioned herein.

In a further aspect, this invention relates to a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt thereof, for use in medical therapy. It will be understood that this invention provides a compound (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a meglumine salt thereof, for use in medical therapy.

In a further aspect, this invention relates to a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt thereof, for use in the treatment of hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy. It will be understood that this invention relates to a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a meglumine salt thereof, for use in the treatment of the diseases mentioned herein.

In a further aspect, this invention relates to a method of treating heart failure which comprises administering to a patient, in particular, a human in need thereof, a therapeutically effective amount of a compound which is (R)-3-(1,4-dimethyl-1H-benzo[d][1,2,3]triazol-5-yl)-3-(3-(((R)-2-ethyl-2,3-dihydropyrido[2,3-][1,4]oxazepin-4(5H)-yl)methyl)-4-methylphenyl)propanoic acid, or a pharmaceutically acceptable salt thereof. It will be understood that this invention relates to a method of treating heart failure which comprises administering to a patient, in particular, human in need thereof, a therapeutically effective amount of a compound which is (R)-3-(1,4-dimethyl-1H-benzo[d][1,2,3]triazol-5-yl)-3-(3-(((R)-2-ethyl-2,3-dihydropyrido[2,3-][1,4]oxazepin-4(5H)-yl)methyl)-4-methylphenyl)propanoic acid, or a meglumine salt thereof.

In a further aspect, this invention relates to the use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt thereof, for the treatment of heart failure. It will be understood that this invention relates to the use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a meglumine salt thereof, for the treatment of heart failure.

In a further aspect, this invention relates to use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt thereof, in the manufacture of a medicament for the treatment of heart failure. It will be understood that this invention relates to a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a meglumine salt thereof, in the manufacture of a medicament for the treatment of heart failure.

In a further aspect, this invention relates to a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt thereof, for use in the treatment of heart failure. It will be understood that this invention relates to a compound which is (R)-3-(1,4-dimethyl-1H-benzo[d][1,2,3]triazol-5-yl)-3-(3-(((R)-2-ethyl-2, 3-dihydropyrido[2,3-f][1,4]oxazepin-4(5H)-yl)methyl)-4-methylphenyl)propanoic acid, or a meglumine salt thereof, for use in the treatment of heart failure.

In one embodiment, the invention is directed to the use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt thereof, in particular, a meglumine salt thereof, as an active therapeutic substance. More specifically, this invention provides for the use of the compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt thereof, in particular, a meglumine salt thereof, for the treatment of a respiratory and non-respiratory disorder, specifically, a disease or disorder recited herein. Accordingly, the invention provides for the use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt thereof, in particular, a meglumine salt thereof, as an active therapeutic substance in the treatment of a human in need thereof with a respiratory and non-respiratory disorder, specifically, a disease or disorder recited herein. Specifically, the invention provides for the use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt thereof, in particular, a meglumine salt thereof, as an active therapeutic substance in the treatment of heart failure.

Additionally, this invention provides for the use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt thereof, in particular, a meglumine salt thereof, for the treatment of hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy. Accordingly, the invention provides for the use of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt thereof, in particular, a meglumine salt thereof, as an active therapeutic substance in the treatment of a patient, in particular, a human in need thereof with of hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy. Specifically, the invention provides for the use of a compound which is (R)-3-(1,4-dimethyl-1H-benzo[d][1,2,3]triazol-5-yl)-3-(3-(((R)-2-ethyl-2,3-dihydropyrido[2,3-][1,4]oxazepin-4(5H)-yl)methyl)-4-methylphenyl)propanoic acid, or a pharmaceutically acceptable salt thereof, in particular, a meglumine salt thereof, as an active therapeutic substance in the treatment of heart failure.

In one aspect, this invention provides for a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, or a pharmaceutically acceptable salt, solvate or hydrate thereof.

Other aspects and advantages of the present invention are described further in the following detailed description of the embodiments thereof.

DETAILED DESCRIPTION OF THE INVENTION

Brief Description of the Figures

FIG. 1 is an X-ray powder diffraction (XRPD) pattern of a crystalline form of the compound of Example 2 which is (R)-3-(1,4-dimethyl-1H-benzo[d][1,2,3]triazol-5-yl)-3-(3-(((R)-2-ethyl-2,3-dihydropyrido[2,3-t][1,4]oxazepin-4(5H)-yl)methyl)-4-methylphenyl)propanoicacid, (–)-1-Deoxy-1-(methylamino)-D-glucitol salt.

In one embodiment, the invention is to a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4 (5H)-yl)methyl)-4-methylphenyl)propanoic acid ("the compound of the invention"), or a pharmaceutically acceptable salt thereof, in particular, a meglumine salt thereof.

The compound of this invention which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl) methyl)-4-methylphenyl)propanoic acid (named using the IUPAC naming convention) is depicted by the following chemical formula:

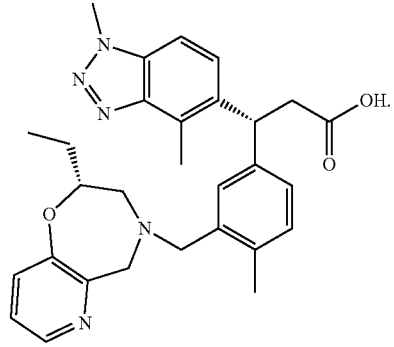

It will be appreciated by the skilled artisan, that the compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, depicted above, has an R-beta stereocenter.

It is to be understood that the references herein to a compound (R)-3-(1,4-dimethyl-1H-benzo[d][1,2,3]triazol-5-yl)-3-(3-(((R)-2-ethyl-2,3-dihydropyrido[2,3-f][1,4] oxazepin-4(5H)-yl)methyl)-4-methylphenyl)propanoic acid or a salt thereof includes the compound as a free form, or as a salt thereof, for example as a pharmaceutically acceptable salt thereof. Thus, in one embodiment, the invention is directed to a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid. In another embodiment, the invention is directed to a salt of a compound of which is (R)-3-(1,4-dimethyl-1H-benzo[d][1,2,3]triazol-5-yl)-3-(3-(((R)-2-ethyl-2,3-dihydropyrido[2,3-t][1,4]oxazepin-4(5H)-yl) methyl)-4-methylphenyl)propanoic acid. In a further embodiment, the invention is directed to a pharmaceutically acceptable salt of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid. In another embodiment, the invention is directed to a compound which is (R)-3-(1,4-dimethyl-1H-benzo[d][1,2,3]triazol-5-yl)-3-(3-(((R)-2-ethyl-2,3-dihydropyrido[2,3-][1,4]oxazepin-4(5H)-yl) methyl)-4-methylphenyl)propanoic acid or a salt thereof. In a further embodiment, the invention is directed to a compound which is (R)-3-(1,4-dimethyl-1H-benzo[d][1,2,3]triazol-5-yl)-3-(3-(((R)-2-ethyl-2,3-dihydropyrido[2,3-f][1,4] oxazepin-4(5H)-yl)methyl)-4-methylphenyl)propanoic acid or a pharmaceutically acceptable salt thereof. A particularly preferred salt of the compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, is the meglumine salt thereof. In still another embodiment, the compound of the invention is a crystalline form of (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoicacid, (−)-1-Deoxy-1-(methylamino)-D-glucitol salt (the meglumine salt of the compound of the invention) characterized by the XPRD pattern of FIG. 1. In yet another embodiment, a particular compound of the invention is a crystalline form (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoicacid, (−)-1-Deoxy-1-(methylamino)-D-glucitol salt, characterized by the diffraction data in Table 2.

The compound which is (R)-3-(1,4-dimethyl-1H-benzo [d][1,2,3]triazol-5-yl)-3-(3-(((R)-2-ethyl-2,3-dihydropyrido [2,3-][1,4]oxazepin-4(5H)-yl)methyl)-4-methylphenyl)propanoic acid, or a pharmaceutically acceptable salt thereof, in particular, a meglumine salt thereof, has potentially beneficial effects based on its ability to regulate the NRF2 pathway and to thereby illicit a response. Hence, this compound is potentially useful in treating the diseases and disorders described herein. In particular, there is evidence that the compound (R)-3-(1,4-dimethyl-1H-benzo[d][1,2,3]triazol-5-yl)-3-(3-(((R)-2-ethyl-2,3-dihydropyrido[2,3-f][1,4] oxazepin-4(5H)-yl)methyl)-4-methylphenyl)propanoic acid, or a pharmaceutically acceptable salt thereof, in particular, a meglumine salt thereof, has enhanced oral bioavailability in dogs (when compared to the S-beta-stereocenter isomer), thereby making it a potentially successful drug in treating heart failure, as well as the other diseases and disorders disclosed herein, in mammals, including humans, particularly for oral administration routes.

Individual stereoisomers of a compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl) methyl)-4-methylphenyl)propanoic acid, contain one or more asymmetric centers and may be resolved by methods known to those skilled in the art. For example, such resolution may be carried out (1) by formation of diastereoisomeric salts, complexes or other derivatives; (2) by selective reaction with a stereoisomer-specific reagent, for example by enzymatic oxidation or reduction; or (3) by gas-liquid or liquid chromatography in a chiral environment, for example, on a chiral support such as silica with a bound chiral ligand or in the presence of a chiral solvent. The skilled artisan will appreciate that where the desired stereoisomer is converted into another chemical entity by one of the separation procedures described above, a further step is required to liberate the desired form. Alternatively, specific stereoisomers may be synthesized by asymmetric synthesis using optically active reagents, substrates, catalysts or solvents, or by converting one enantiomer to the other by asymmetric transformation.

As used herein, "pharmaceutically acceptable" refers to those compounds (including salts), materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

The skilled artisan will appreciate that pharmaceutically acceptable salts of the compound which is (R)-3-(1,4-dimethyl-1H-benzo[d][1,2,3]triazol-5-yl)-3-(3-(((R)-2-ethyl-2, 3-dihydropyrido[2,3-t][1,4]oxazepin-4(5H)-yl)methyl)-4-methylphenyl)propanoic acid may be prepared. These pharmaceutically acceptable salts may be prepared in situ during the final isolation and purification of the compound, or by separately treating the purified compound in its free acid or free base form with a suitable base or acid, respectively.

The compound of the invention contains an acidic functional group and is, therefore, capable of forming pharmaceutically acceptable base addition salts by treatment with a suitable base. Representative pharmaceutically acceptable base addition salts include, but are not limited to, aluminium, 2-amino-2-(hydroxymethyl)-1,3-propanediol (TRIS, tromethamine), arginine, benethamine (N-benzylphenethylamine), benzathine (N,N'-dibenzylethylenediamine), bis-(2-hydroxyethyl)amine, bismuth, calcium, chloroprocaine, choline, clemizole (1-p chlorobenzyl-2-pyrrolildine-1'-ylmethylbenzimidazole), cyclohexylamine, dibenzylethylenediamine, diethylamine, diethyltriamine, dimethylamine, dimethylethanolamine, dopamine, ethanolamine, ethylenediamine, L-histidine, iron, isoquinoline, lepidine, lithium, lysine, magnesium, meglumine (N-methylglucamine), piperazine, piperidine, potassium, procaine, quinine, quinoline, sodium, strontium, t-butylamine, and zinc.

The compound of the invention also contains a basic functional group and is therefore capable of forming pharmaceutically acceptable acid addition salts by treatment with a suitable acid. Representative pharmaceutically acceptable acid addition salts include, but are not limited to, 4-acetamidobenzoate, acetate, adipate, alginate, ascorbate, aspartate, benzenesulfonate (besylate), benzoate, bisulfate, bitartrate, butyrate, calcium edetate, camphorate, camphorsulfonate (camsylate), caprate (decanoate), caproate (hexanoate), caprylate (octanoate), cinnamate, citrate, cyclamate, digluconate, 2,5-dihydroxybenzoate, disuccinate, dodecylsulfate (estolate), edetate (ethylenediaminetetraacetate), estolate (lauryl sulfate), ethane-1,2-disulfonate (edisylate), ethanesulfonate (esylate), formate, fumarate, galactarate (mucate), gentisate (2,5-dihydroxybenzoate), glucoheptonate (gluceptate), gluconate, glucuronate, glutamate, glutarate, glycerophosphorate, glycolate, hexylresorcinate, hippurate, hydrabamine (N,N'-di(dehydroabietyl)-ethylenediamine), hydrobromide, hydrochloride, hydroiodide, hydroxynaphthoate, isobutyrate, lactate, lactobionate, laurate, malate, maleate, malonate, mandelate, methanesulfonate (mesylate), methylsulfate, mucate, naphthalene-1,5-disulfonate (napadisylate), naphthalene-2-sulfonate (napsylate), nicotinate, nitrate, oleate, palmitate, p-aminobenzenesulfonate, p-aminosalicyclate, pamoate (embonate), pantothenate, pectinate, persulfate, phenylacetate, phenylethylbarbiturate, phosphate, polygalacturonate, propionate, p-toluenesulfonate (tosylate), pyroglutamate, pyruvate, salicylate, sebacate, stearate, subacetate, succinate, sulfamate, sulfate, tannate, tartrate, teoclate (8-chlorotheophyllinate), thiocyanate, triethiodide, undecanoate, undecylenate, and valerate.

Pharmaceutically acceptable salts include, amongst others, those described in Berge, J. Pharm. Sci., 1977, 66, 1-19, or those listed in P H Stahl and C G Wermuth, editors, *Handbook of Pharmaceutical Salts; Properties, Selection and Use, Second Edition* Stahl/Wermuth: Wiley-VCH/VHCA, 2011 (see http://www.wiley.com/WileyCDA/WileyTitle/productCd-3906390519.html).

The compound which is (R)-3-(1,4-dimethyl-1H-benzo[d][1,2,3]triazol-5-yl)-3-(3-(((R)-2-ethyl-2,3-dihydropyrido[2,3-t][1,4]oxazepin-4(5H)-yl)methyl)-4-methylphenyl)propanoic acid may exist in solid or liquid form. In the solid state, it may exist in crystalline or noncrystalline form, or as a mixture thereof. The skilled artisan will appreciate that pharmaceutically acceptable solvates may be formed from crystalline compounds wherein solvent molecules are incorporated into the crystalline lattice during crystallization. Solvates may involve non-aqueous solvents such as, but not limited to, ethanol, isopropanol, DMSO, acetic acid, ethanolamine, or ethyl acetate, or they may involve water as the solvent that is incorporated into the crystalline lattice. Solvates wherein water is the solvent incorporated into the crystalline lattice are typically referred to as "hydrates." Hydrates include stoichiometric hydrates as well as compositions containing variable amounts of water.

The skilled artisan will further appreciate that the compound of the invention exists in crystalline form, and may exhibit polymorphism (i.e., the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound conditions or used in crystallizing/recrystallizing the compound. For example, changes in temperature, pressure, or solvent may result in polymorphs. In addition, one polymorph may spontaneously convert to another polymorph under certain conditions.

It is well known and understood to those skilled in the art that the apparatus employed, humidity, temperature, orientation of the powder crystals, and other parameters involved in obtaining a powder X-ray diffraction (XRPD) pattern may cause some variability in the appearance, intensities, and positions of the lines in the diffraction pattern. A powder X-ray diffraction pattern that is "substantially in accordance" with that of the FIGURE provided herein is a XRPD pattern that would be considered by one skilled in the art to represent a compound possessing the same crystal form as the compound that provided the XRPD pattern of the FIGURE. For example, the XRPD pattern may be identical to that of FIG. 1, or more likely it may be somewhat different. Such a XRPD pattern may not necessarily show each of the lines of the diffraction patterns presented herein, and/or may show a slight change in appearance, intensity, or a shift in position of said lines resulting from differences in the conditions involved in obtaining the data. A person skilled in the art is capable of determining if a sample of a crystalline compound has the same form as, or a different form from, a form disclosed herein by comparison of their XRPD patterns. For example, one skilled in the art can overlay a XRPD pattern of a sample of a crystalline form of (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoicacid, (−)-1-Deoxy-1-(methylamino)-D-glucitol salt with the XRPD pattern of FIG. 1, and using expertise and knowledge in the art, readily determine whether the XRPD pattern of the sample is substantially in accordance with the XRPD pattern of FIG. 1. If the XRPD pattern is substantially in accordance with FIG. 1, the sample form can be readily and accurately identified as having the same form as the crystalline form of (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoicacid, (−)-1-Deoxy-1-(methylamino)-D-glucitol salt described herein. Similarly, a person skilled in the art is capable of determining if a given diffraction angle (expressed in °2θ) obtained from a XRPD pattern is at about the same position as a recited value.

The subject invention also includes isotopically-labelled compounds, which are identical to those recited in Formula (I) and following, but for the fact that one or more atoms are replaced by an atom having an atomic mass or mass number different from the atomic mass or mass number usually found in nature. Examples of isotopes that can be incorporated into compounds of the invention and pharmaceutically acceptable salts thereof include isotopes of hydrogen, carbon, nitrogen, oxygen, phosphorous, sulphur, fluorine, iodine, and chlorine, such as $^{2}H$, $^{3}H$, $^{11}C$, $^{13}C$, $^{14}C$, $^{15}N$, $^{17}O$, $^{18}O$, $^{31}P$, $^{32}P$, $^{35}S$, $^{18}F$, $^{36}Cl$, $^{123}I$ and $^{125}I$.

The compound of the invention and pharmaceutically acceptable salts thereof contain the aforementioned isotopes and/or other isotopes of other atoms are within the scope of the present invention. Isotopically-labelled compounds of the present invention, for example those into which radioactive isotopes such as $^{3}H$, $^{14}C$ are incorporated, are useful in drug and/or substrate tissue distribution assays. Tritiated, i.e., $^{3}H$, and carbon-14, i.e., $^{14}C$, isotopes are particularly preferred for their ease of preparation and detectability. $^{11}C$ and $^{18}F$ isotopes are particularly useful in PET (positron emission tomography), and $^{125}I$ isotopes are particularly useful in SPECT (single photon emission computerized tomography), all useful in brain imaging. Further, substitution with heavier isotopes such as deuterium, i.e., $^{2}H$, can afford certain therapeutic advantages resulting from greater metabolic stability, for example increased in vivo half-life or reduced dosage requirements and, hence, may be preferred in some circumstances. Isotopically labeled compounds of Formula (I) and following of this invention can generally be prepared by carrying out the procedures disclosed in the Schemes and/or in the Examples below, by substituting a readily available isotopically labeled reagent for a non-isotopically labeled reagent.

Compound Preparation

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art; examples of which may be found in T. Greene and P. Wuts, *Protecting Groups in*

*Chemical Synthesis* (3rd ed.), John Wiley & Sons, NY (1999). In some instances, a substituent may be specifically selected to be reactive under the reaction conditions used. Under these circumstances, the reaction conditions convert the selected substituent into another substituent that is either useful as an intermediate compound or is a desired substituent in a target compound.

The synthesis of the compound of the invention, and pharmaceutically acceptable salts thereof, may be accomplished as outlined below in Schemes 1-4. Abbreviations are as defined in the Examples section. Starting materials are commercially available or are made from commercially available starting materials using methods known to those skilled in the art.

Scheme 1

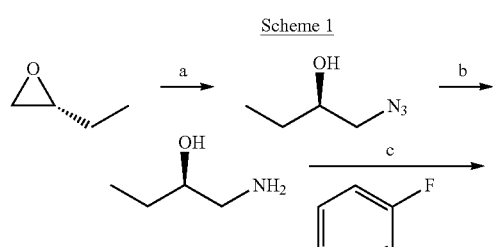

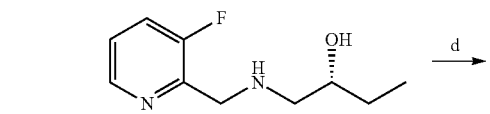

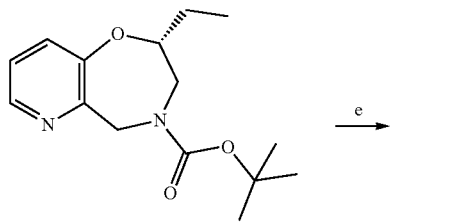

Conditions: a) NaN₃; b) H₂, Pd/C; c) MgSO₄, NaBH₄; d) KOtBu, Boc₂O; e) HCl

Scheme 2

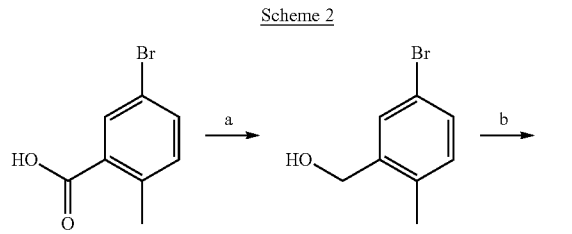

-continued

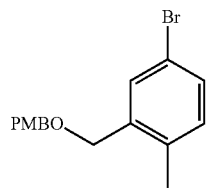

Conditions: a) BH₃—DMS; b) NaH, PMB—Cl

Scheme 3

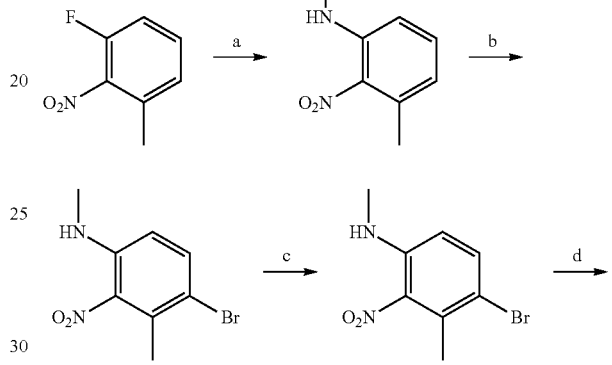

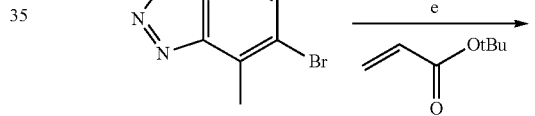

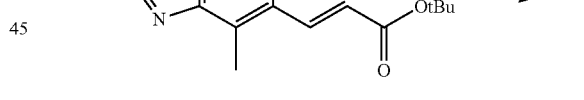

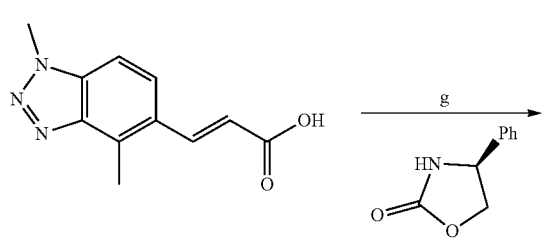

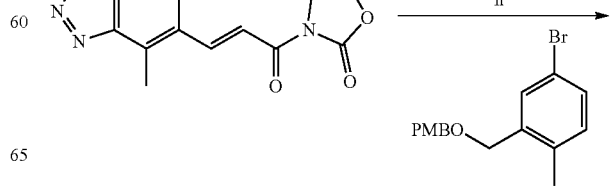

17
-continued
18
-continued
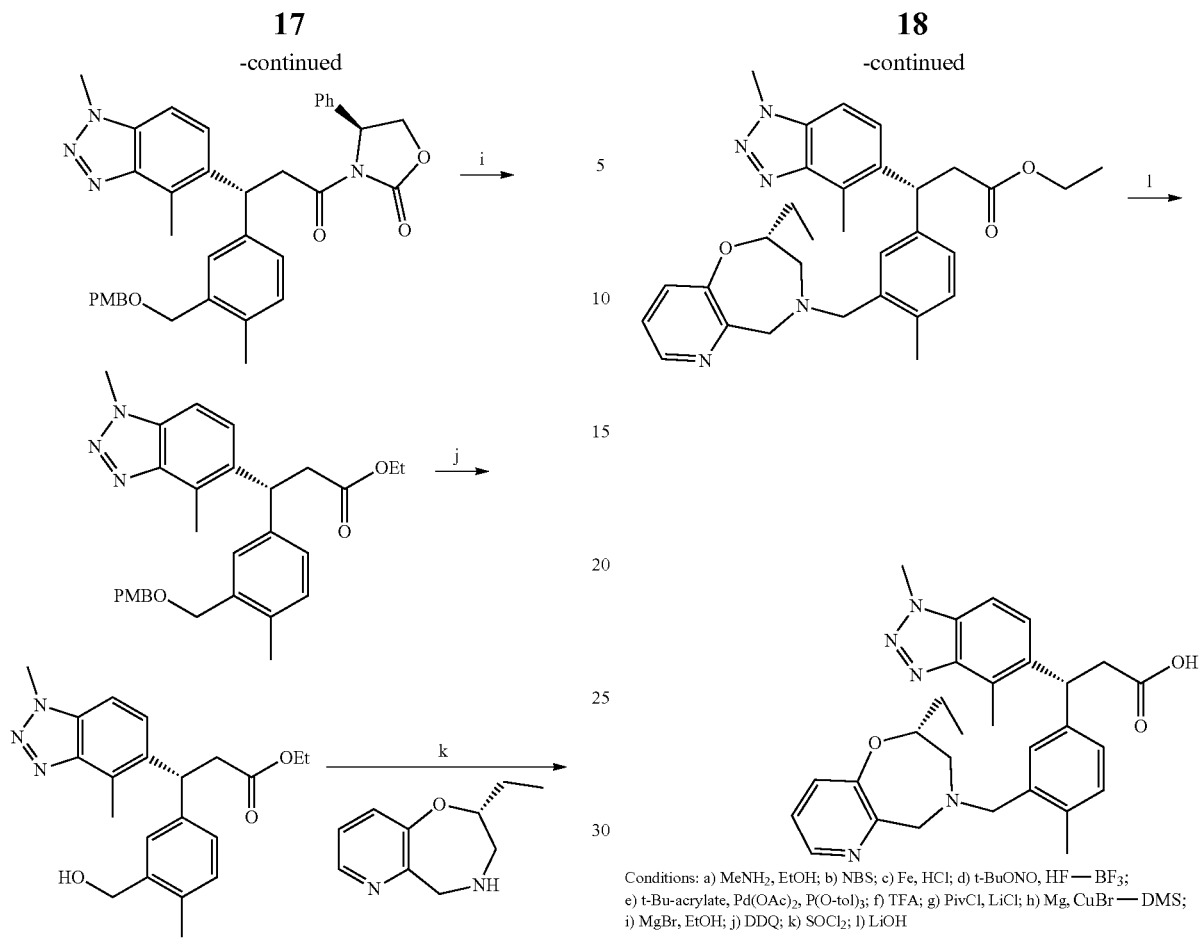
Conditions: a) MeNH₂, EtOH; b) NBS; c) Fe, HCl; d) t-BuONO, HF—BF₃; e) t-Bu-acrylate, Pd(OAc)₂, P(O-tol)₃; f) TFA; g) PivCl, LiCl; h) Mg, CuBr—DMS; i) MgBr, EtOH; j) DDQ; k) SOCl₂; l) LiOH
Scheme 4
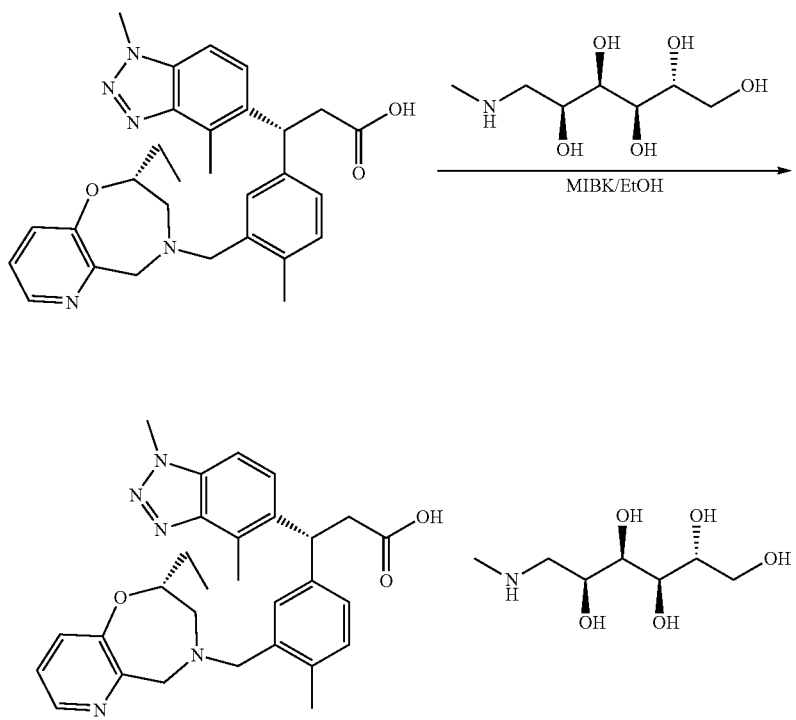

Biological Activity

As stated above, the compound of the invention is an NRF2 activator, and is useful in the treatment of human diseases that exhibit oxidative stress components such as respiratory and non-respiratory disorders, including COPD, asthma, ALI, ARDS, fibrosis, chronic asthma, acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, AKI, kidney disease or malfunction seen during kidney transplantation, Pulmonary Arterial Hypertension, hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy atherosclerosis, PD, AD, FA, ALS, MS, inflammatory bowel disease, colon cancer, neovascular (dry) AMD and neovascular (wet) AMD, eye injury, FECD, uveitis or other inflammatory eye conditions, NASH, toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, high altitude sickness, SCD, Progeria and CRS.

In addition, the compound of the invention, or a pharmaceutically acceptable salt thereof, in particular, a meglumine salt thereof, is useful in treating hypertension, heart failure, acute coronary syndrome, myocardial infarction, myocardial repair, cardiac remodelling, cardiac arrhythmias.

The biological activity of the compound of the invention, or a pharmaceutically acceptable salt thereof, in particular, a meglumine salt thereof, can be determined using any suitable assay for determining the activity of a candidate compound as an NRF2 activator, as well as tissue and in vivo models.

The biological activity of the compound which is of the invention, or a pharmaceutically acceptable salt thereof, in particular, a meglumine salt thereof is demonstrated by the following tests.

BEAS-2B NQO1 MTT Assay

NAD(P)H:quinone oxidoreductase 1 (NQO1), also called DT diaphorase, is a homodimeric FAD-containing enzyme that catalyzes obligatory NAD(P)H-dependent two-electron reductions of quinones and protects cells against the toxic and neoplastic effects of free radicals and reactive oxygen species arising from one-electron reductions. The transcription of NQO1 is finely regulated by NRF2, and thus NQO1 activity is a good marker for NRF2 activation. On day one, frozen BEAS-2B cells (ATCC) are thawed in a water bath, counted, and re-suspended at a concentration of 250,000 cells/mL. Fifty microliters of cells are plated in 384 well black clear-bottomed plates. Plates are incubated at 37° C., 5% $CO_2$ overnight. On day two, plates are centrifuged and 50 nL of compound or controls are added to the cells. Plates are then incubated at 37° C., 5% $CO_2$ for 48 hours. On day four, medium is aspirated from the plate and crude cell lysates are made by adding 13 uL of 1× Cell Signaling Technologies lysis buffer with 1 Complete, Mini, EDTA-free Protease Inhibitor Tablet (Roche) for each 10 mL of lysis buffer. After lysis plates are incubated for 20 minutes at room temperature. Two microliters of lysate are removed for use in Cell Titer Glo assay (Promega) and MTT cocktail is prepared (Prochaska et. al. 1998) for measurement of NQO1 activity. Fifty microliters of MTT cocktail is added to each well, plate is centrifuged, and analyzed on an Envision plate reader (Perkin Elmer) using Absorbance 570 nm label for 30 minutes. Product formation is measured kinetically and the $EC_{50}$ of NQO1 specific activity induction is calculated by plotting the change in absorbance (Delta OD/min) versus the log of compound concentration followed by 3-parameter fitting.

NRF2-Keap1 FP Assay One model for the NRF2-Keap1 interaction is through two binding sites in the Neh2 domain on NRF2. The two sites are referred to as the DLG binding motif (latch domain, uM affinity) and the ETGE binding motif (hinge domain, nM affinity). The Keap1 protein consists of an N-terminal region (NTR), a broad complex, tramtrack, and brick a brac domain (BTB), an intervening region (IVR), a double glycine repeat domain (DGR or Kelch), and a C-terminal region. The DLG and ETGE motifs of NRF2's Neh2 domain bind to the Kelch domain of Keap1 at different affinities. In the Keap1 Kelch fluorescence polarization (FP) assay, a TAMRA-labeled 16 mer peptide (AFFAQLQLDEETGEFL) containing the ETGE motif of NRF2 and the Kelch domain (321-609) of Keap1 is used. The assay determines if a compound interferes with the binding between Keap1 (361-609) and the TAMRA-labeled peptide. Binding of TAMRA-labeled NRF2 peptide to Keap1 (321-609) results in a high FP signal. If a compound interferes with the binding between the peptide and the protein, it will cause the assay signal to decrease. Thus, assay signal is inversely proportional to binding inhibition.

FP Assay:

100 nl of 100× compound dose response curves (serial 3-fold dilutions) in DMSO are stamped using an Echo liquid handling system (Labcyte) into 384-well low volume black assay plates (Greiner, #784076), with DMSO in columns 6 and 18. The top concentration of compound is located in columns 1 and 13. Keap1 (321-609) is diluted to 40 nM (2×) in 1× assay buffer (50 mM Tris, pH 8.0, 100 mM NaCl, 5 mM $MgCl_2$, 1 mM DTT, 2 mM CHAPS, and 0.005% BSA) and 5 ul is added using a Multidrop Combi (Thermo Electron Corporation) equipped with a metal tip dispenser to all wells of the compound plate, except column 18. Column 18 receives only 5 ul of assay buffer. Immediately, 5 uL of 16 nM (2×) of Tamra labeled peptide (AFFAQLQLDEET-GEFL, $21^{st}$ Century Biochemicals) is added to all wells of the plate. The plates are spun at 500 rpm for 1 min, incubated for 1 hr at room temperature, and read on an Analyst GT (Molecular Devices) equipped with excitation (530/25 nm) and emission (580/10 nm) filters designed for Tamra probes. A 561 nm dichroic mirror is also used in the Analyst. The final assay concentrations of Keap1 (321-609) and Tamra labelled peptide are 20 nM and 8 nM, respectively. Fluorescence measurements, represented as mP, are used in the transformation of the data. Compound activity is calculated based on percent inhibition, normalized against controls in the assay (Control 1 contains the Tamra peptide and Keap1 (321-609) together (0% response) and control 2 contains the Tamra peptide alone (100% response)). Data analysis is handled using the software package Abase XE (Surrey, United Kingdom. The % inhibition values are calculated by the equation:

100−(100*((compound response-average control 2)/(average control 1-average control2))). For calculation of $pIC_{50}$s, Abase XE uses a four parameter equation.

NRF2-Keap1 TR-FRET Assay

In the NRF2-Keap1 TR-FRET (time-resolved fluorescence resonance energy transfer) assay, full length NRF2 protein and full length Keap1 protein (Keap1 exists a dimer) are used. The assay detects the ability of compound to displace the binding of FlagHis-tagged Keap1 with biotinylated, Avi-tagged NRF2 protein. Biotin-NRF2 binds to streptavidin-europium (a component of the detection mix) and Keap1-FlagHis is recognized by anti-Flag APC (allophycocyanin) antibody (also a component of the detection mix). If binding occurs between the two proteins, there will be an energy transfer from the Eu+3 (donor) at 615 nm to the APC (acceptor) at 665 nm. A potential Keap1 inhibitor will cause a reduction in the TR-FRET signal by interfering with the binding of Keap1 to NRF2.

One hundred nanoliters of 100× compound dose response curves (serial 3-fold dilutions) in DMSO are stamped using an Echo liquid handling system (Labcyte) into 384-well, low volume, black assay plates (Greiner, #784076), with DMSO in columns 6 and 18. The top concentration of compound is located in columns 1 and 13. All reagents are diluted in assay buffer (50 mM Tris, pH 8.0, 5 mM MgCl2, 100 mM NaCl, 0.005% BSA, 1 mM DTT, and 2 mM CHAPS). The BSA, DTT, and CHAPS are added to the assay buffer on the day of assay. Using a Multidrop Combi (Thermo Electron Corporation) equipped with a metal tip dispenser, 5 ul of 25 nM Keap1-FlagHis protein is added to all wells of the compound plate, with the exception of the wells in column 18. Wells in column 18 receive 5 ul of assay buffer instead. Plates are centrifuged at 500 rpm for 1 minute, covered with a plate lid, and incubated at 37° C. for 2.25 hours. Plates are then removed from the incubator and allowed to cool to RT for 15 minutes. Five microliters of 50 nM biotin-NRF2 protein is then added to all wells of the plates and the plates are spun at 500 rpm for 1 minute, followed by incubating at 4° C. for 1.25 hours. The plates are then allowed to warm to RT for 15 minutes, followed by the addition of 10 ul of detection mix (1 nM Streptavidin Eu+ W1024 and 5 ug/ml mouse anti-DYKDDDDK IgG conjugated to SureLight APC antibody; both from Columbia Biosciences) to all wells. Plates are spun at 500 rpm for 1 minute, incubated for 1 hour at RT, and read on an Envision plate reader using a 320 nm excitation filter and 615 nm and 665 nm emission filters. Compound response (% inhibition) and potency (pIC50) are calculated based on the ratio of the two emissions (665 nm/615 nm) and then the transformed data is normalized against controls in the assay (control 1=1% DMSO in the presence of NRF2 and Keap1 protein and control 2=1% DMSO in the absence of protein). Data analysis is handled using the software package Abase XE (Surrey, United Kingdom). The % inhibition values are calculated from the ratio (transformed) data by the equation:

100−(100*(compound response−average control 2)/
(average control 1−average control2)).

For calculation of pIC50s, Abase XE uses a four parameter equation.

Dog PK Study

All studies were conducted after review by the GSK Institutional Animal Care and Use Committee and in accordance with the GSK Policy on the Care, Welfare and Treatment of Laboratory Animals. A pre-study health examination that included a physical exam and complete blood count was performed on the animals prior to use on study. A catheter was temporarily placed in a cephalic or saphenous vein for sample collection on the study day. The animals were fasted overnight prior to dosing; food provided after the 4-hour blood sample was collected. The intravenous and oral solution pharmacokinetic studies were carried out using a non-crossover design; a total of four male beagle dogs were used, two per route of administration.

The dose for intravenous administration was prepared as a cassette of up to five test compounds in 20% Cavitron™ and 5% DMSO. The intravenous dose formulation was filtered through a 0.22-micron polytetrafluoroethylene (PTFE) filter prior to administration. The dose for oral solution administration was prepared as a cassette of up to five compounds in 6% Cavitron™ and 5% DMSO and was filtered through a 0.22 micron VWR PTFE filter prior to administration.

Each animal received a nominal dose of 1 mg/kg/compound (4 mL/kg dose volume) either as a 60-minute intravenous infusion or as an oral gavage. Blood samples (approximately 0.25 mL each) were collected from a cephalic or saphenous vein. Blood samples from animals that received the intravenous dose were collected prior to dosing and at target times of 15, 30, 45, 60 (before termination of the infusion), 62, 65, 75, 90, 120, 180, 240, 360, 480, 600, and 1440 minutes following the initiation of the intravenous infusion. For animal that received the oral dose, blood samples were collected prior to dosing and at target times of 5, 15, 30, 45, 60, 90, 120, 180, 240, 360, 480, 600, and 1440 minutes following oral gavage. Plasma was isolated from blood by centrifugation and a 30-μL aliquot was transferred to a non-heparinized tube, quick frozen on solid carbon dioxide and stored at approximately −80° C. until analyzed by liquid chromatography/tandem mass spectroscopy (LC/MS/MS) for test compound concentration.

Pharmacokinetic parameters were calculated using non-compartmental methods with Phoenix WinNonlin version 6.1.0. All parameters were calculated using actual blood sampling times and actual dosages for each animal. The extrapolated area under the curve ($AUC_{0-inf}$) was determined using unweighted linear regression analysis of at least three log transformed concentrations visually assessed to be on the linear portion of the terminal elimination slope. Oral solution bioavailability was calculated in a non-crossover fashion using the mean intravenous dose and $AUC_{0-inf}$ values from the two intravenously dosed animals.

Results of the assays conducted and described above are summarized in Table 1 below.

TABLE 1

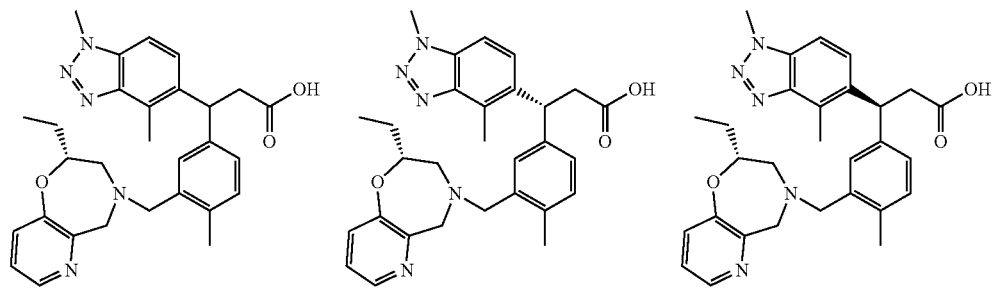

TABLE 1-continued

| Compound Structure | Beta-stereocenter 50/50 mixture | Formula (I) R-beta-stereocenter isomer | S-beta-stereocenter isomer |
| --- | --- | --- | --- |
| NRF2-KEAP1 FP $IC_{50}$ | 63 nM | 40 nM | 50 nM |
| NRF2-KEAP1 TR-FRET $IC_{50}$ | 25 nM | 16 nM | 12 nM |
| NRF2 BEAS-2B NQO1 $EC_{50}$ | 20 nM | 20 nM | 16 nM |
| Rat PK $F_{po}$ | 177% | 129% | 78% |
| Dog PK $F_{po}$ | Not determined | 52% | 11% |

Demonstration of oral bioavailability (>30%) in two species, rodent and non-rodent, is a key criterion used in the selection of compounds for progression as it provides confidence of oral bioavailability in humans. Bioavailability is generally classified into two buckets, less than or greater than 30%. A bioavailability of <30% represents a significant risk in assessing viability as a medicament, signaling that you would not have bioavailability in humans.

One of skill in the art would understand that values of >100% for oral bioavailability are not 'real' but reflect assay variability. Therefore, the fact that some values in Table 1 are reported over 100% reflects a measurement error of the assay and inherent PK variability from animal to animal. Thus, it would be understood that the ~2-fold differences in rat bioavailability are considered within the error of the assay and indistinguishable. However, the ~5-fold difference in the dog oral bioavailability (the compound of the invention demonstrated 52% oral bioavailability in a dog while the S-isomer demonstrated 11%) is a clear and unexpected difference result particularly given the similarity in structure and similar rat bioavailability.

Methods of Use

The compound of the invention, or a pharmaceutically acceptable salt, in particular, a meglumine salt, thereof, is useful in treating respiratory and non-respiratory disorders, including COPD, asthma, ALI, ARDS, fibrosis, chronic asthma, acute asthma, lung disease secondary to environmental exposures, acute lung infection, chronic lung infection, al antitrypsin disease, cystic fibrosis, autoimmune diseases, diabetic nephropathy, chronic kidney disease, sepsis-induced acute kidney injury, AKI, kidney disease or malfunction seen during kidney transplantation, Pulmonary Arterial Hypertension, hypertension, heart failure, acute coronary syndrome, myocardial infarction, myocardial repair, cardiac remodeling, cardiac arrhythmias, heart failure with preserved ejection fraction, heart failure with reduced ejection fraction, diabetic cardiomyopathy atherosclerosis, PD, AD, FA, ALS, MS, inflammatory bowel disease, colon cancer, neovascular (dry) AMD and neovascular (wet) AMD, eye injury, FECD, uveitis or other inflammatory eye conditions, NASH, toxin-induced liver disease (e.g., acetaminophen-induced hepatic disease), viral hepatitis, cirrhosis, psoriasis, dermatitis/topical effects of radiation, immunosuppression due to radiation exposure, Preeclampsia, high altitude sickness, SCD, Progeria and CRS. Said disorders are treated by administering to a patient, in particular, a human, in need thereof, a compound of the invention, or a pharmaceutically acceptable salt, in particular, a meglumine salt, thereof. Accordingly, in another aspect the invention is directed to methods of treating such conditions.

In one embodiment, the compound of the invention, or a pharmaceutically acceptable salt, in particular, a meglumine salt, thereof, is useful in treating respiratory disorders including COPD, asthma, including chronic asthma and acute asthma.

In one embodiment, the compound of the invention, or a pharmaceutically acceptable salt, in particular, a meglumine salt, thereof, is useful in treating hypertension, heart failure, acute coronary syndrome, myocardial infarction, myocardial repair, cardiac remodeling, cardiac arrhythmias, heart failure with preserved ejection fraction, heart failure with reduced ejection fraction and diabetic cardiomyopathy.

The methods of treatment of the invention comprise administering a therapeutically effective amount of a compound of the invention, or a pharmaceutically acceptable salt, in particular, a meglumine salt, thereof, to a patient, in particular, a human in need thereof. A therapeutically "effective amount" is intended to mean that amount of a compound that, when administered to a patient in need of such treatment, is sufficient to effect treatment, as defined herein. Thus, e.g., a therapeutically effective amount of a compound of the invention, or a pharmaceutically acceptable salt thereof, is a quantity of an inventive agent that, when administered to a patient, e.g., a human, in need thereof, is sufficient to modulate and/or activate NRF2 such that a disease condition which is mediated by that NRF2-activity is reduced, alleviated or prevented. The amount of a given compound that will correspond to such an amount will vary depending upon factors such as the potency ($pIC_{50}$), efficacy ($EC_{50}$), and the biological half-life of the particular compound, disease condition and its severity, the identity (e.g., age, size and weight) of the patient in need of treatment, but can nevertheless be routinely determined by one skilled in the art. Likewise, the duration of treatment and the time-period of administration (time-period between dosages and the timing of the dosages, e.g., before/with/after meals) of the compound will vary according to the identity of the mammal in need of treatment (e.g., weight), the particular compound and its properties (e.g., pharmacokinetic properties), disease or disorder and its severity and the specific composition and method being used, but can nevertheless be determined by one of skill in the art.

It will be understood that a compound of the invention, or a pharmaceutically acceptable salt thereof, is administered in a "safe and effective amount' which means an amount of the compound sufficient to treat the patient's condition but low enough to avoid serious side effects (at a reasonable benefit/risk ratio) within the scope of sound medical judgment. A safe and effective amount of a compound will vary with the particular compound chosen (e.g. consider the potency, efficacy, and half-life of the compound); the route of administration chosen; the condition being treated; the severity of the condition being treated; the age, size, weight, and physical condition of the patient being treated; the medical history of the patient to be treated; the duration of the treatment; the nature of concurrent therapy; the desired therapeutic effect; and like factors, but can nevertheless be routinely determined by the skilled artisan.

As used herein, "treat" in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

Accordingly, it will be understood that the method of treatment of the invention, includes preventing any of the diseases or conditions disclosed herein.

The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "patient" refers to a human or other animal.

The compound of the invention, or a pharmaceutically acceptable salt thereof, may be administered by any suitable route of administration, including both systemic administration and topical administration. Systemic administration includes oral administration, parenteral administration, transdermal administration, rectal administration, and administration by inhalation. Parenteral administration refers to routes of administration other than enteral, transdermal, or by inhalation, and is typically by injection or infusion. Parenteral administration includes intravenous, intramuscular, and subcutaneous injection or infusion. Inhalation refers to administration into the patient's lungs whether inhaled through the mouth or through the nasal passages. Topical administration includes application to the skin as well as intraocular, otic, intravaginal, and intranasal administration.

The compound of the invention, or a pharmaceutically acceptable salt thereof, may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention, or a pharmaceutically acceptable salt thereof, depend on the pharmacokinetic properties of the compound, or a pharmaceutically acceptable salt thereof, such as absorption, distribution, and half-life, which can be determined by the skilled artisan. In addition, suitable dosing regimens, including the duration such regimens are administered, for a compound of the invention, or a pharmaceutically acceptable salt thereof, depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Typical daily dosages may vary depending upon the particular route of administration chosen. Typical dosages for oral administration range from 1 mg to 1000 mg per person per day. Preferred dosages are 1-500 mg once daily, more preferred is 1-100 mg per person per day. IV dosages range form 0.1-000 mg/day, preferred is 0.1-500 mg/day, and more preferred is 0.1-100 mg/day. Inhaled daily dosages range from 10 ug-10 mg/day, with preferred 10 ug-2 mg/day, and more preferred 50 uug-500 ug/day.

Additionally, the compound of the invention, or a pharmaceutically acceptable salt thereof, may be administered as a prodrug. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (c) modify the transportation or distribution of the compound in vivo; (d) modify the solubility of the compound in vivo; and (e) overcome a side effect or other difficulty encountered with the compound. Typical functional derivatives used to prepare prodrugs include modifications of the compound that are chemically or enzymatically cleaved in vivo. Such modifications, which include the preparation of phosphates, amides, ethers, esters, thioesters, carbonates, and carbamates, are well known to those skilled in the art.

Compositions

The compound of the invention, or a pharmaceutically acceptable salt thereof, will normally, but not necessarily, be formulated into pharmaceutical compositions prior to administration to a patient. Accordingly, in another aspect the invention is directed to pharmaceutical compositions comprising a compound of the invention and one or more pharmaceutically-acceptable excipient.

The pharmaceutical compositions of the invention may be prepared and packaged in bulk form wherein a safe and effective amount of a compound of the invention can be extracted and then given to the patient such as with powders or syrups. Alternatively, the pharmaceutical compositions of the invention may be prepared and packaged in unit dosage form wherein each physically discrete unit contains a safe and effective amount of a compound of the invention. When prepared in unit dosage form, the pharmaceutical compositions of the invention typically contain from 1 mg to 1000 mg.

The pharmaceutical compositions of the invention typically contain only the compound of the invention, or a pharmaceutically acceptable salt thereof. In addition, the pharmaceutical compositions of the invention may optionally further comprise one or more additional pharmaceutically active compounds.

As used herein, "pharmaceutically-acceptable excipient" means a pharmaceutically acceptable material, composition or vehicle involved in giving form or consistency to the pharmaceutical composition. Each excipient must be compatible with the other ingredients of the pharmaceutical composition when commingled such that interactions which would substantially reduce the efficacy of the compound of the invention when administered to a patient and interactions which would result in pharmaceutical compositions that are not pharmaceutically acceptable are avoided. In addition, each excipient must of course be of sufficiently high purity to render it pharmaceutically-acceptable.

The compound of the invention and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; (2) parenteral administration such as sterile solutions, suspensions, and powders for reconstitution; (3) transdermal administration such as transdermal patches; (4) rectal administration such as suppositories; (5) inhalation such as dry powders, aerosols, suspensions, and solutions; and (6) topical administration such as creams, ointments, lotions, solutions, pastes, sprays, foams, and gels.

Suitable pharmaceutically-acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting of the compound of the invention once administered to the patient from one organ, or portion of the body, to another organ, or portion of the body. Certain pharmaceutically-acceptable excipients may be chosen for their ability to enhance patient compliance.

Suitable pharmaceutically-acceptable excipients include the following types of excipients: bacteriostats, solutes, propellants, thickening agents, diluents, fillers, binders, disintegrants, lubricants, glidants, granulating agents, coating agents, wetting agents, solvents, co-solvents, suspending agents, emulsifiers, sweeteners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically-acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in *Remington's Pharmaceutical Sciences* (Mack Publishing Company).

In one aspect, the invention is directed to a solid oral dosage form such as a tablet or capsule comprising a safe and effective amount of a compound of the invention and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesium stearate, calcium stearate, and talc.

In another aspect, the invention is directed to a dosage form adapted for administration to a patient parenterally including subcutaneous, intramuscular, intravenous or intradermal. Pharmaceutical formulations adapted for parenteral administration include aqueous and non-aqueous sterile injection solutions which may contain anti-oxidants, buffers, bacteriostats, and solutes that render the formulation isotonic with the blood of the intended recipient; and aqueous and non-aqueous sterile suspensions which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules, and tablets.

In another aspect, the invention is directed to a dosage form adapted for administration to a patient by inhalation. For example, the compound of the invention may be inhaled into the lungs as a dry powder, an aerosol, a suspension, or a solution.

Dry powder compositions for delivery to the lung by inhalation typically comprise a compound of the invention as a finely divided powder together with one or more pharmaceutically acceptable excipients as finely divided powders. Pharmaceutically acceptable excipients particularly suited for use in dry powders are known to those skilled in the art and include lactose, starch, mannitol, and mono-, di-, and polysaccharides.

The dry powder compositions for use in accordance with the present invention are administered via inhalation devices. As an example, such devices can encompass capsules and cartridges of for example gelatin, or blisters of, for example, laminated aluminum foil. In various embodiments, each capsule, cartridge or blister may contain doses of composition according to the teachings presented herein. Examples of inhalation devices can include those intended for unit dose or multi-dose delivery of composition, including all of the devices set forth herein. As an example, in the case of multi-dose delivery, the formulation can be pre-metered (e.g., as in Diskus®, see GB2242134, U.S. Pat. Nos. 6,032,666, 5,860,419, 5,873,360, 5,590,645, 6,378,519 and 6,536,427 or Diskhaler, see GB 2178965, 2129691 and 2169265, U.S. Pat. Nos. 4,778,054, 4,811,731, 5,035,237) or metered in use (e.g. as in Turbuhaler, see EP 69715, or in the devices described in U.S. Pat. No. 6,321,747). An example of a unit-dose device is Rotahaler (see GB 2064336). In one embodiment, the Diskus® inhalation device comprises an elongate strip formed from a base sheet having a plurality of recesses spaced along its length and a lid sheet peelably sealed thereto to define a plurality of containers, each container having therein an inhalable formulation containing the compound optionally with other excipients and additive taught herein. The peelable seal is an engineered seal, and in one embodiment the engineered seal is a hermetic seal. Preferably, the strip is sufficiently flexible to be wound into a roll. The lid sheet and base sheet will preferably have leading end portions which are not sealed to one another and at least one of the leading end portions is constructed to be attached to a winding means. Also, preferably the engineered seal between the base and lid sheets extends over their whole width. The lid sheet may preferably be peeled from the base sheet in a longitudinal direction from a first end of the base sheet.

A dry powder composition may also be presented in an inhalation device which permits separate containment of two different components of the composition. Thus, for example, these components are administrable simultaneously but are stored separately, e.g. in separate pharmaceutical compositions, for example as described in WO 03/061743 A1 WO 2007/012871 A1 and/or WO2007/068896. In one embodiment, an inhalation device permitting separate containment of components is an inhaler device having two peelable blister strips, each strip containing pre-metered doses in blister pockets arranged along its length, e.g., multiple containers within each blister strip. Said device has an internal indexing mechanism which, each time the device is actuated, peels open a pocket of each strip and positions the blisters so that each newly exposed dose of each strip is adjacent to the manifold which communicates with the mouthpiece of the device. When the patient inhales at the mouthpiece, each dose is simultaneously drawn out of its associated pocket into the manifold and entrained via the mouthpiece into the patient's respiratory tract. A further device that permits separate containment of different components is DUOHALER™ of Innovata. In addition, various structures of inhalation devices provide for the sequential or separate delivery of the pharmaceutical composition(s) from the device, in addition to simultaneous delivery.

Aerosols may be formed by suspending or dissolving a compound of the invention in a liquefied propellant. Suitable propellants include halocarbons, hydrocarbons, and other liquefied gases. Representative propellants include: trichlorofluoromethane (propellant 11), dichlorodifluoromethane (propellant 12), dichlorotetrafluoroethane (propellant 114), tetrafluoroethane (HFA-134a), 1,1-difluoroethane (HFA-152a), difluoromethane (HFA-32), pentafluoroethane (HFA-12), heptafluoropropane (HFA-227a), perfluoropropane, perfluorobutane, perfluoropentane, butane, isobutane, and pentane. Aerosols comprising a compound of the invention will typically be administered to a patient via a metered dose inhaler (MDI). Such devices are known to those skilled in the art.

The aerosol may contain additional pharmaceutically acceptable excipients typically used with multiple dose inhalers such as surfactants, lubricants, cosolvents and other excipients to improve the physical stability of the formulation, to improve valve performance, to improve solubility, or to improve taste.

Suspensions and solutions comprising a compound of the invention may also be administered to a patient via a nebulizer. The solvent or suspension agent utilized for nebulization may be any pharmaceutically acceptable liquid such as water, aqueous saline, alcohols or glycols, e.g., ethanol, isopropyl alcohol, glycerol, propylene glycol, polyethylene glycol, etc. or mixtures thereof. Saline solutions utilize salts which display little or no pharmacological activity after administration. Both organic salts, such as alkali metal or ammonium halogen salts, e.g., sodium chloride, potassium chloride or organic salts, such as potassium, sodium and ammonium salts or organic acids, e.g., ascorbic acid, citric acid, acetic acid, tartaric acid, etc. may be used for this purpose.

Other pharmaceutically acceptable excipients may be added to the suspension or solution. The compound of the invention may be stabilized by the addition of an inorganic acid, e.g., hydrochloric acid, nitric acid, sulfuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

The compound of the invention, or a pharmaceutically acceptable salt thereof, may be used in combination with one or more other agents which may be useful in the prevention or treatment of allergic disease, inflammatory disease, autoimmune disease, for example; antigen immunotherapy, antihistamines, corticosteroids, (e.g., fluticasone propionate, fluticasone furoate, beclomethasone dipropionate, budesonide, ciclesonide, mometasone furoate, triamcinolone, flunisolide), NSAIDs, leukotriene modulators (e.g. montelukast, zafirlukast, pranlukast), iNOS inhibitors, tryptase inhibitors, IKK2 inhibitors, p38 inhibitors, Syk inhibitors, protease inhibitors such as elastase inhibitors, integrin antagonists (e.g., beta-2 integrin antagonists), adenosine A2a agonists, mediator release inhibitors such as sodium chromoglycate, 5-lipoxygenase inhibitors (zyflo), DP1 antagonists, DP2 antagonists, PI3K delta inhibitors, ITK inhibitors, LP (lysophosphatidic) inhibitors or FLAP (5-lipoxygenase activating protein) inhibitors (e.g. sodium 3-(3-(tert-butylthio)-1-(4-(6-ethoxypyridin-3-yl)benzyl)-5-((5-methylpyridin-2-yl) methoxy)-1H-indol-2-yl)-2,2-dimethylpropanoate), bronchodilators (e.g., muscarinic antagonists, beta-2 agonists), methotrexate, and similar agents; monoclonal antibody therapy such as anti-IgE, anti-TNF, anti-IL-5, anti-IL-6, anti-IL-12, anti-IL-1 and similar agents; cytokine receptor therapies e.g. etanercept and similar agents; antigen nonspecific immunotherapies (e.g. interferon or other cytokines/chemokines, chemokine receptor modulators such as CCR3, CCR4 or CXCR2 antagonists, other cytokine/chemokine agonists or antagonists, TLR agonists and similar agents).

The compound may also be used in combination with agents for aiding transplantation including Cyclosporines, Tacrolimus, Mycophenolate mofetil, Prednisone, Azathioprine, Sirolimus, Daclizumab, Basiliximab, or OKT3.

The compound may also be used in combination with agents for Diabetes: metformin (biguanides), meglitinides, sulfonylureas, DPP-4 inhibitors, Thiazolidinediones, Alpha-glucosidase inhibitors, Amylin mimetics, Incretin mimetics and insulin.

The compound may be used in combination with antihypertensives such as diuretics, ACE inhibitors, ARBS, calcium channel blockers, and beta blockers.

One embodiment of the invention encompasses combinations comprising one or two other therapeutic agents. It will be clear to a person skilled in the art that, where appropriate, the other therapeutic ingredient(s) may be used in the form of salts, for example as alkali metal or amine salts or as acid addition salts, or prodrugs, or as esters, for example lower alkyl esters, or as solvates, for example hydrates to optimize the activity and/or stability and/or physical characteristics, such as solubility, of the therapeutic ingredient. It will be clear also that, where appropriate, the therapeutic ingredients may be used in optically pure form.

The combinations referred to above may conveniently be presented for use in the form of a pharmaceutical formulation and thus pharmaceutical formulations comprising a combination as defined above together with a pharmaceutically acceptable diluent or carrier represent a further aspect of the invention. As used herein, "carrier" or "drug carrier" is any substrate used in the process of drug delivery which serves to improve the selectivity, effectiveness, and/or safety of drug administration. Drug carriers are primarily used to control the release of a drug into systemic circulation.

The individual compounds of such combinations may be administered either sequentially or simultaneously in separate or combined pharmaceutical formulations. In one embodiment, the individual compounds will be administered simultaneously in a combined pharmaceutical formulation. Appropriate doses of known therapeutic agents will readily be appreciated by those skilled in the art.

The invention thus provides, in a further aspect, a pharmaceutical composition comprising a combination of a compound of the invention, or a pharmaceutically acceptable salt thereof, together with another therapeutically active agent.

EXAMPLES

The invention will now be described by reference to the following examples which are merely illustrative and are not to be construed as a limitation of the scope of the present invention. All temperatures are given in degrees Celsius, all solvents are highest available purity and all reactions run under anhydrous conditions in an argon (Ar) or nitrogen ($N_2$) atmosphere where necessary.

Analtech Silica Gel GF and E. Merck Silica Gel 60 F-254 thin layer plates were used for thin layer chromatography. Both flash and gravity chromatography were carried out on silica gel 230-400, 100-200 & 60-120. The CombiFlash® system used for purification in this application was purchased from Isco, Inc. CombiFlash® purification was carried out using prepacked silica gel columns, a detector with UV wavelength at 254 nm and a variety of solvents or solvent combinations.

Analytical HPLC was run using an Agilent system or Waters Alliance HPLC with 2996 PDA detector, Waters Acquity UPLC-MS or Agilent Infinity 1290 with PDA or conducted on a Sunfire C18 column, alternative on XSELECT CSH C18 column using reverse phase chromatography with a $CH_3CN$ and water gradient with 0.1% formic acid modifier (added to each solvent) and basic conditions used a basic modifier, usually 5 mM ammonium bicarbonate or 10 mM ammonium bicarbonate in water adjusted pH to 10 with ammonia solution. The compound was analyzed by LCMS using a Shimadzu LC system with UV 214 nm wavelength detection and $H_2O$—$CH_3CN$ gradient elution (4-95% over 1.9 min.) acidified to 0.02% TFA. The reversed-phase column was a 2.1×20 mm Thermo Hypersil Gold C18 (1.9 u particles) at 50° C. The single quadrupole MS detector was either a Sciex 150EX or a Waters ZQ operated in positive-ion. Alternatively, LC-MS was determined using either a PE Sciex Single Quadrupole 150EX LC-MS, or Waters ZQ Single Quadrupole, Waters 3100 Single Quadrupole, Agilent 6130 SQD or Agilent 6120 Single Quadrupole LC-MS instruments. The compound is analyzed using a reverse phase column, e.g., Thermo Hypersil Gold C18, Luna C18, Sunfire C18 and/or Zorbax C18 eluted using a gradient of $CH_3CN$ and water with a low percentage of an acid modifier such as 0.02% or 0.1% TFA.

Analytical Chiral SFC was run using a Thar/Waters SFC system with variable wavelength UV detection. A variety of chiral SFC columns, e.g. Chiralpak IA, IB, IC, ID, IF, IG, AY, AD, OD, C2, AS, OJ, CCL4 were used in the purification. The compounds are eluted using supercritical fluid $CO_2$ and co-solvents, such as MeOH, EtOH, IPA, and combination of these solvent in different ratio based on the compound selectivity. Modifiers (0.1% to 0.4% of TFA, $NH_4OH$, DEA, TEA) would be used as needed.

Celite® is a filter aid composed of acid-washed diatomaceous silica, and is a registered trademark of Manville Corp., Denver, Colo. Isolute® is a functionalized silica gel based sorbent, and is a registered trademark of Biotage AB Corp., Sweden.

Nuclear magnetic resonance spectra were recorded at 400 MHz using a Bruker AVANCE 400 or Brucker DPX400 spectrometer or Varian MR400 spectrometer. $CHCl_3$-d is deuteriochloroform, DMSO-$d_6$ is hexadeuteriodimethylsulfoxide, and MeOD is tetradeuteriomethanol, $CD_2Cl_2$ is deuteriodichloromethane. Chemical shifts are reported in parts per million ($\delta$) downfield from the internal standard tetramethylsilane (TMS) or calibrated to the residual proton signal in the NMR solvent (e.g., $CHCl_3$ in $CDCl_3$). Abbreviations for NMR data are as follows: s=singlet, d=doublet, t=triplet, q=quartet, m=multiplet, dd=doublet of doublets, dt=doublet of triplets, app=apparent, br=broad. J indicates the NMR coupling constant measured in Hertz.

Heating of reaction mixtures with microwave irradiation was carried out on a Biotage Initiator® microwave reactor, typically employing the high absorbance setting.

Cartridges or columns containing polymer based functional groups (acid, base, metal chelators, etc) can be used as part of compound workup. The "amine" columns or cartridges are used to neutralize or basify acidic reaction mixtures or products. These include $NH_2$ Aminopropyl SPE-ed SPE Cartridges available from Applied Separations and diethylamino SPE cartridges available from United Chemical Technologies, Inc.

| Table of Abbreviations | |
|---|---|
| [Rh(cod)Cl]2 or [RhCl(cod)]2: di-µ-chlorido-bis[η2,η2-(cycloocta-1,5-diene)rhodium | MeCN: acetonitrile |
| ®T3P: 2,4,6-tripropyl-1,3,5,2,4,6-trioxatriphosphorinane 2,4,6-trioxide | MeI: methyl iodide |
| ° C.: degree Celsius | MeOH: methanol |
| AcOH: acetic acid | mg: milligram(s) |
| ADDP: (E)-diazene-1,2-diylbis(piperidin-1-ylmethanone) | $MgCl_2$: magnesium chloride |
| aq = aqueous | $MgSO_4$: magnesium sulfate |
| BINAP: 2,2'-bis(diphenylphosphino)-1,1'-binaphthalene | MHz: megahertz |
| CDI: Carbonyl dimidazole | min: minute(s) |
| $CH_2Cl_2$: dichloromethane | mL: milliliter(s) |
| $CH_3CN$: acetonitrile | mmol: millimole(s) |
| $CH_3CN$: acetonitrile | MS: mass spectroscopy |
| $CHCl_3$: chloroform | $N_2$: nitrogen gas |
| $Cs_2CO_3$: cesium carbonate | $Na_2CO_3$: sodium carbonate |
| DBU: 1,8-diazabicyclo[5.4.0]undec-7-ene | $Na_2SO_4$: sodium sulfate |
| | $NaBH_4$: sodium borohydride |
| DCE: dichloroethane | $NaBH_3CN$ or $NaCNBH3$: sodium cyanoborohydride |

| Table of Abbreviations | |
|---|---|
| DCM: dichloromethane | NaCl: sodium chloride |
| DDQ: 2,3-Dichloro-5,6-dicyano-1,4-benzoquinone | |
| DIPEA or DIEA: diisopropylethylamine | NaH: sodium hydride |
| DME: dimethyl ether | NaHCO$_3$: sodium bicarbonate |
| DMF: N,N-dimethylformamide | NaHMDS: sodium hexamethyldisilazane |
| DMF-DMA or DMF-dimethyl acetal: N,N-dimethylformaide-dimethyl acetal | NaHSO$_4$: sodium bisulfate |
| DMSO: dimethyl sulfoxide | NaOAc: sodium acetate |
| EDC: 1-ethyl-3-(3-dimethylaminopropyl)carbodiimide | NaOH: sodium hydroxide |
| Et$_2$O: diethyl ether | NBS: N-Bromosuccinimide |
| Et$_3$N: triethylamine | nBuLi: n-butyl lithium |
| EtOAc: ethyl acetate | NH$_4$Cl: ammonium chloride |
| EtOH: ethanol | NMR: nuclear magnetic resonance |
| g: gram(s) | P(tBu)$_3$: tri-t-butyl phosphine |
| h: hour(s) | Pd(PPh$_3$)$_4$: tetrakistriphenylphosphine palladium |
| HATU: O-(7-azabenzotriazol-1-yl)-N,N,N',N'-tetramethyluronium hexafluorophosphate | Pd/C: pallidium on carbon |
| HBTU: N,N,N',N'-tetramethyl-O-(1H-benzotriazol-1-yl)uronium hexafluorophosphate | Pd$_2$(dba)$_3$: tris(dibenzylideneacetone)-dipalladium(0) |
| HCl: hydrochloric acid | PdCl$_2$(dppf) or Pd(dppf)Cl2: [1,1'-bis(diphenylphosphino)-ferrocene]dichloropalladium(II) |
| HOAt: 1-hydroxy-7-azabenzotriazole | Petrol: petroleum ether |
| HPLC: high performance liquid chromatography | PS-PPh$_3$: polymer supported triphenylphosphine |
| IPA: isopropyl alcohol | PtO$_2$: platinum(IV) oxide |
| KOtBu: potassium tert-butoxide | |
| K$_2$CO$_3$: potassium carbonate | RT: room temperature |
| KOAc: Potassium acetate | T$_3$P: 2,4,6-tripropyl-1,3,5,2,4,6-trioxatriphosphorinane-2,4,6-trioxide solution |
| LAH: lithium aluminum hydride | TEA: triethylamine |
| LC: liquid chromatography | TFA: trifluoroacetic acid |
| LC-MS: liquid chromatography-mass spectroscopy | TFFH: Tetrafluoroformamidinium hexafluorophosphate |
| LiBH$_4$: lithium borohydride | THF: tetrahydrofuran |
| LiHMDS: lithium hexamethyldisilazane | triflic anhydride: trifluoromethanesulfonic anhydride |
| LiOH: lithium hydroxide | TsOH: p-toluenesulfonic acid |
| M: molar | wt %: weight percent |

Example 1: (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid 1(a): (R)-1-azidobutan-2-ol

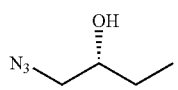

To a round bottom flask equipped with a reflux condenser was added (R)-2-ethyloxirane (26.0 g, 361 mmol), sodium azide (28.1 g, 433 mmol) and ammonium chloride (23.15 g, 433 mmol) followed by a solution of ethanol (200 mL) and water (200 mL). The reaction mixture was heated at 100° C. for 24 hr. The reaction mixture was cooled, the ethanol removed under reduced pressure and the residual aqueous layer extracted with diethyl ether (3×250 mL). The organic extracts were combined, washed with brine, dried over sodium sulfate, filtered and the solvent evaporated under reduced pressure to afford an oil. The oil was purified by silica gel chromatography (0-10% MeOH/DCM) to afford (R)-1-azidobutan-2-ol (19.8 g, 172 mmol, 47.7% yield). $^1$H NMR (CHCl$_3$-d) δ: 3.64-3.76 (m, 1H), 3.35-3.46 (m, 1H), 3.20-3.34 (m, 1H), 2.19 (s, 1H), 1.47-1.60 (m, 2H), 0.90-1.06 (m, 3H)

1(b): (R)-1-aminobutan-2-ol

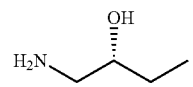

To a solution of (R)-1-azidobutan-2-ol (19.80 g, 172 mmol) in ethanol (250 mL) was added 10% palladium on carbon (1.830 g, 17.20 mmol) and the suspension was placed under a hydrogen atmosphere for 72 hr. Additional 10% palladium on carbon (1.830 g, 17.20 mmol) was added at 24 & 48 hr time points. The reaction mixture was filtered through celite and then evaporated under reduced pressure to afford a light-yellow oil (R)-1-aminobutan-2-ol (13.5 g, 151 mmol, 88% yield). $^1$H NMR (CHCl$_3$-d) δ: 3.43 (m, 1H), 2.77 (m, 1H), 2.64 (br. s., 3H), 2.52 (m, 1H), 1.36-1.48 (m, 2H), 0.87-0.96 (m, 3H).

1(c): (R)-1-(((3-fluoropyridin-2-yl)methyl)amino)butan-2-ol

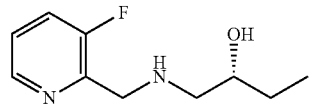

To a solution of (R)-1-aminobutan-2-ol (3.70 g, 41.5 mmol) in methanol (150 mL) was added 3-fluoropicolinaldehyde (4.67 g, 37.4 mmol) followed by magnesium sulfate (4.50 g, 37.4 mmol) and the reaction mixture was stirred at 0° C. for 1 hr. The reaction mixture was filtered through celite and washed with methanol (300 ml). Sodium borohydride (1.413 g, 37.4 mmol) was added in two portions to the filtrate and the reaction mixture was stirred at room temperature for 30 min. The reaction mixture was quenched with 10% sodium bicarbonate solution and the methanol evaporated under reduced pressure. The remaining aqueous phase was extracted with ethyl acetate (3×125 mL) and the combined organic extracts were washed with brine, dried over sodium sulfate, filtered and the solvent evaporated under reduced pressure. The crude residue was purified by silica gel chromatography (0-100%/3:1 ethyl acetate:ethanol/hexanes) to afford a yellow oil (R)-1-(((3-fluoropyridin-2-yl)methyl)amino)butan-2-ol (5.3 g, 24.06 mmol, 58.0% yield). $^1$H NMR (CHCl$_3$-d) δ: 8.36-8.45 (m, 1H), 7.37-7.45 (m, 1H), 7.22-7.32 (m, 1H), 4.10-4.16 (m, 2H), 3.68-3.77 (m, 1H), 2.89 (m, 1H), 2.64 (m, 1H), 1.43-1.55 (m, 2H), 0.90-1.02 (m, 3H). LC-MS: m/z 199.2 (M+H)$^+$

1(d): (R)-tert-butyl 2-ethyl-2,3-dihydropyrido[2,3-f][1,4]oxazepine-4(5H)-carboxylate

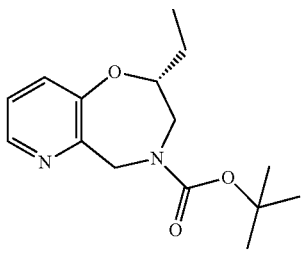 [SMILES: CC[C@@H]1CN(C(=O)OC(C)(C)C)Cc2ncccc2O1]

To a solution of (R)-1-(((3-fluoropyridin-2-yl)methyl)amino)butan-2-ol (5.20 g, 26.2 mmol) in dimethyl sulfoxide (100 mL) was added potassium tert-butoxide (3.68 g, 32.8 mmol) and the reaction mixture was stirred at 90° C. for 45 min. The reaction mixture was cooled to room temperature to afford a deep red-colored solution. Boc-anhydride (6.09 mL, 26.2 mmol) was added and the reaction mixture was allowed to stir for 18 hr. The reaction mixture was diluted with ethyl acetate (500 mL) and the organic phase washed with water (4×200 mL), brine, dried over sodium sulfate, filtered and the solvent evaporated under reduced pressure. The crude residue was purified by silica gel chromatography (0-50% ethyl acetate/hexanes) to afford an orange oil (R)-tert-butyl 2-ethyl-2,3-dihydropyrido[2,3-f][1,4]oxazepine-4(5H)-carboxylate (4.84 g, 17.39 mmol, 66.3% yield). $^1$H NMR (DMSO-d$_6$) δ: 8.17 (m, 1H), 7.36 (m, 1H), 7.24 (m, 1H), 4.49-4.76 (m, 2H), 3.93 (br. s., 1H), 3.47-3.74 (m, 2H), 1.52-1.66 (m, 2H), 1.36 (br. s., 4H), 1.25 (s, 5H), 0.96-1.07 (m, 3H). LC-MS: m/z 279.2 (M+H)$^+$.

1(e): (R)-2-ethyl-2,3,4,5-tetrahydropyrido[2,3-f][1,4]oxazepine, hydrochloride

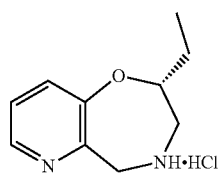

To a solution of (R)-tert-butyl 2-ethyl-2,3-dihydropyrido[2,3-f][1,4]oxazepine-4(5H)-carboxylate (4.84 g, 17.39 mmol) in 1,4-dioxane (20 mL), at room temperature, was added 4N HCl in dioxane (100 mL, 400 mmol) and the reaction mixture was stirred at room temperature for 2 hr. The solvent was evaporated under reduced pressure and azeotroped with diethyl ether (3×) to afford a cream solid (R)-2-ethyl-2,3,4,5-tetrahydropyrido[2,3-f][1,4]oxazepine, hydrochloride (3.55 g, 16.54 mmol, 95% yield). $^1$H NMR (DMSO-d$_6$) δ: 9.95-10.36 (m, 2H), 8.38 (m, 1H), 7.66 (m, 1H), 7.51 (m, 1H), 4.39-4.57 (m, 2H), 4.04-4.18 (m, 1H), 3.47-3.60 (m, 1H), 3.24-3.40 (m, 1H), 1.69 (m, 2H), 1.05 (m, 3H). LC-MS: m/z 179.2 (M+H)$^+$

1(f): (5-bromo-2-methylphenyl)methanol

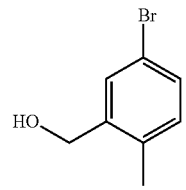

A stirred solution of 5-bromo-2-methylbenzoic acid (100 g, 465 mmol) in tetrahydrofuran (1.2 L) was cooled in an ice bath to 0° C. 2N borane-methyl sulfide complex in THF (302 mL, 605 mmol) was added dropwise via additional funnel over 90 min. The reaction mixture was allowed to warm to room temperature and was stirred for 24 hr. Reaction mixture was cooled to 0° C., quenched with methanol (200 ml) and was stirred for 1 hr. The solvents were removed under reduced pressure and the resultant oil was partitioned between diethyl ether (1 L) and 1N HCl (1 L). The layers were separated and the aqueous extracted with diethyl ether (2×500 mL). The combined organic extracts were washed with 1N HCl (2×500 ml), brine, dried over sodium sulfate, filtered and concentrated to afford a soft yellow solid (5-bromo-2-methylphenyl)methanol (97 g, 482 mmol, 104% yield). $^1$H NMR (CHCl$_3$-d) δ: 7.54 (s, 1H), 7.33 (d, J=8.0 Hz, 1H), 7.05 (d, J=8.3 Hz, 1H), 4.66 (s, 2H), 2.28 (s, 3H), 1.99 (br. s., 1H). LC-MS: m/z 183.0 (M−OH)$^+$

1(g): 4-bromo-2-(((4-methoxybenzyl)oxy)methyl)-1-methylbenzene

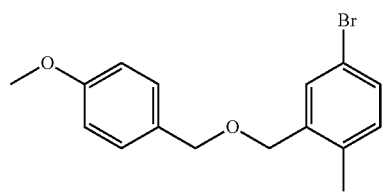 [SMILES: COc1ccc(COCc2cc(Br)ccc2C)cc1]

A stirred suspension of 60% sodium hydride in mineral oil (24.83 g, 621 mmol) in tetrahydrofuran (800 mL) was cooled to 0° C. A solution of (5-bromo-2-methylphenyl)methanol (96 g, 477 mmol) in tetrahydrofuran (100 ml) was added dropwise over 90 minutes and was then stirred for 15 minutes. 1-(chloromethyl)-4-methoxybenzene (71.5 mL, 525 mmol) was added dropwise over 10 minutes. The resultant was allowed to warm to room temperature and was stirred for 24 hr. After 3 hr, DMF (200 ml) was added to the reaction mixture. After 24 hr, piperazine (8.23 g, 95 mmol) was added and the mixture stirred for 1 hr. The reaction mixture was cooled to 0° C. and quenched with water (200 ml) and then diluted with diethyl ether (1.5 L) and water (1 L) and the layers were separated. The aqueous layer was extracted with diethyl ether (500 mL). The combined organic extracts were washed with water (2×500 mL), 1N HCl (2×500 mL), brine, dried over sodium sulfate and concentrated under reduced pressure to afford a yellow oil. The oil was purified by silica gel chromatography (0-20% ethyl acetate/hexane) to afford a colorless oil 4-bromo-2-(((4-methoxybenzyl)oxy)methyl)-1-methylbenzene (145 g, 451 mmol, 95% yield). $^1$H NMR (DMSO-d$_6$) δ: 7.49 (m, 1H), 7.38 (m, 1H), 7.24-7.33 (m, 2H), 7.14 (m, 1H), 6.88-6.97 (m, 2H), 4.48 (m, 4H), 3.70 (s, 3H), 2.20 (s, 3H). LC-MS: m/z=319.0 (M+H)⁺

1(h): N,3-dimethyl-2-nitroaniline

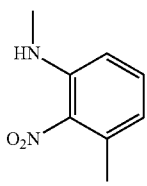

1-fluoro-3-methyl-2-nitrobenzene (50 g, 322 mmol) was dissolved in ethanol (250 mL) and 40% methanamine in water (98 mL, 1128 mmol) was added. The reaction mixture was heated to reflux for 8 hr and then cooled back to room temperature. The reaction mixture was filtered to afford an orange solid N,3-dimethyl-2-nitroaniline (47.9 g, 288 mmol, 89% yield). ¹H NMR (DMSO-d₆) δ: 7.29 (t, J=8.0 Hz, 1H), 6.70 (d, J=8.5 Hz, 1H), 6.55 (d, J=7.3 Hz, 1H), 6.51 (d, J=4.3 Hz, 1H), 2.78 (d, J=4.8 Hz, 3H), 2.30 (s, 3H). LC-MS: m/z 167.2 (M+H)⁺

1(i): 4-bromo-N,3-dimethyl-2-nitroaniline

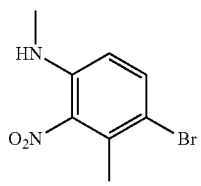

N,3-dimethyl-2-nitroaniline (47.9 g, 288 mmol) was dissolved in N,N-dimethylformamide (250 mL). The mixture was cooled to 5° C. N-Bromosuccinimide (51.3 g, 288 mmol) dissolved in 150 mL N,N-dimethylformamide was added dropwise via an addition funnel and was stirred at room temperature for 24 hr. The reaction mixture was poured into water (1.5 L) and filtered to afford an orange solid 4-bromo-N,3-dimethyl-2-nitroaniline (73.5 g, 300 mmol, 99% yield). ¹H NMR (DMSO-d₆) δ: 7.56 (d, J=9.3 Hz, 1H), 6.66 (d, J=9.3 Hz, 1H), 6.26 (d, J=4.5 Hz, 1H), 2.73 (d, J=4.8 Hz, 3H), 2.25 (s, 3H). LC-MS: m/z 245.0 (M+H)⁺

1(j): 4-bromo-N1,3-dimethylbenzene-1,2-diamine

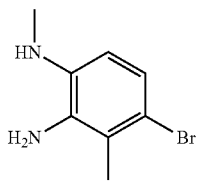

To a solution of 4-bromo-N,3-dimethyl-2-nitroaniline (78.4 g, 320 mmol) in acetic acid (500 mL) and ethanol (500 mL) at 00° C. was added iron powder (89 g, 1600 mmol) followed by 2N HCl (320 mL, 640 mmol). The mixture was stirred for 1 hr and then filtered through celite and the filtrate concentrated to remove the majority of ethanol. The residue was diluted with ethyl acetate (800 ml) and water (800 ml) and the layers separated. The organic extract was washed with water (500 mL), 10% sodium bicarbonate solution (500 mL), brine and concentrated under reduced pressure to afford a red oil 4-bromo-N1,3-dimethylbenzene-1,2-diamine (67 g, 311 mmol, 97% yield). ¹H NMR (DMSO-d₆) δ: 6.75 (d, J=8.5 Hz, 1H), 6.22 (d, J=8.5 Hz, 1H), 4.48-4.90 (m, 2H), 2.69 (s, 3H), 2.17 (s, 3H). LC-MS: m/z=215.2 (M+H)

1(k): 5-bromo-1,4-dimethyl-1H-benzo[d][1,2,3]triazole

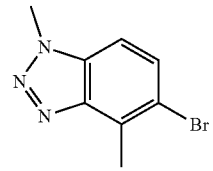

Tert-butyl nitrite (61.5 mL, 467 mmol, 90% tech grade) and tetrafluoroboric acid (97 mL, 623 mmol, 48% aqueous solution) were dissolved in 50 mL of acetonitrile and cooled to 0° C. Then, a solution of 4-bromo-N1,3-dimethylbenzene-1,2-diamine (67 g, 311 mmol) dissolved in a solution of acetonitrile (200 ml) and tetrafluoroboric acid, (97 mL, 623 mmol, 48% aqueous solution) was added slowly, dropwise so that the internal temperature never rose above 5° C. The reaction mixture was stirred at 5° C. for 2 hr and then room temperature for 1 hr. The reaction mixture was poured into a stirred solution of sodium hydroxide (100 g, 2500 mmol) in water (4 L). Sodium chloride was added until the solution reached saturation. The resulting solid was collected by filtration and washed with water (2×3 L), air dried and purified by silica gel column chromatography (25-100% ethyl acetate/hexanes) to afford a light-yellow solid 5-bromo-1,4-dimethyl-1H-benzo[d][1,2,3]triazole (61 g, 267 mmol, 86% yield). ¹H NMR (DMSO-d₆) δ: 7.66 (m, 2H), 4.30 (s, 3H), 2.70 (s, 3H). LC-MS: m/z=226 (M+H)⁺

1(l): tert-butyl (E)-3-(1,4-dimethyl-1H-benzo[d][1,2,3]triazol-5-yl)acrylate

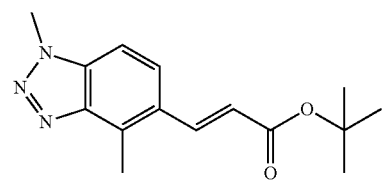 [SMILES: Cc1c(/C=C/C(=O)OC(C)(C)C)ccc2c1nnn2C]

A solution of 5-bromo-1,4-dimethyl-1H-benzo[d][1,2,3]triazole (100 g, 443 mmol) and N,N-dimethylformamide (1000 mL) was purged with nitrogen for 30 min. Tri-o-tolylphosphine (27.0 g, 89 mmol), Pd(OAc)₂ (9.95 g, 44.3 mmol), and potassium carbonate (184 g, 1330 mmol) and tert-butyl acrylate (130 mL, 886 mmol) were added and the reaction mixture was heated at 100° C. for 24 hr under a nitrogen atmosphere. The reaction mixture was cooled to room temperature, diluted with water (1 L) and ethyl acetate (1 L) and the layers separated. The aqueous layer was extracted with ethyl acetate (2×1 L) and then the combined organic extracts were washed with water (2×), brine, dried over sodium sulfate, filtered and the solvent evaporated under reduced pressure. The crude dark solid was triturated with diethyl ether, filtered and dried under vacuum to afford a light-brown solid tert-butyl (E)-3-(1,4-dimethyl-1H-benzo[d][1,2,3]triazol-5-yl)acrylate (109.3 g, 89% yield). $^1$H NMR (DMSO-d$_6$) δ: 7.89-8.00 (m, 2H), 7.67 (m, 1H), 6.54 (d, J=15.8 Hz, 1H), 4.29 (s, 3H), 2.79 (s, 3H), 1.51 (s, 9H). LCMS: m/z 274.2 [M+H]$^+$ 1(m): (E)-3-(1,4-dimethyl-1H-benzo[d][1,2,3]triazol-5-yl)acrylic acid

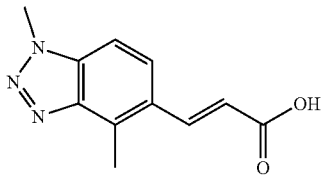 [SMILES: Cc1c(/C=C/C(=O)O)ccc2c1nnn2C]

To a solution of tert-butyl (E)-3-(1,4-dimethyl-1H-benzo[d][1,2,3]triazol-5-yl)acrylate (107 g, 391 mmol) in dichloromethane (300 mL) was added cold trifluoroacetic acid (250 mL) and the reaction mixture was stirred at room temperature for 2 hr. The solvent was evaporated under reduced pressure and then azeotroped with chloroform. The resulting solid was triturated in diethyl ether to afford a beige solid (E)-3-(1,4-dimethyl-1H-benzo[d][1,2,3]triazol-5-yl)acrylic acid (80 g, 368 mmol, 94% yield). $^1$H NMR (DMSO-d$_6$) δ: 7.90-8.02 (m, 2H), 7.69 (m, 1H), 6.55 (d, J=16.1 Hz, 1H), 4.30 (s, 3H), 2.80 (s, 3H) LC-MS: m/z 218.2 [M+H]$^+$ 1(n): (S,E)-3-(3-(1,4-dimethyl-1H-benzo[d][1,2,3]triazol-5-yl)acryloyl)-4-phenyloxazolidin-2-one

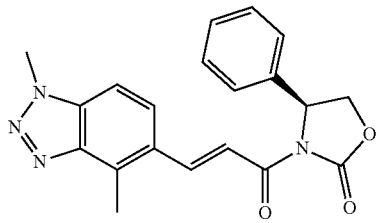 [SMILES: Cc1c(/C=C/C(=O)N2C(=O)OC[C@@H]2c2ccccc2)ccc2c1nnn2C]

To a suspension of (E)-3-(1,4-dimethyl-1H-benzo[d][1,2,3]triazol-5-yl)acrylic acid (82 g, 376 mmol) in tetrahydrofuran (1.5 L) was added triethylamine (131 mL, 939 mmol). The reaction mixture was cooled to −25° C. and pivaloyl chloride (46 ml, 376 mmol) was added dropwise and stirred for 30 min at −25° C. Lithium chloride (17.52 g, 413 mmol) was added in one-portion, followed by (S)-4-phenyloxazolidin-2-one (58.8 g, 361 mmol) and the reaction mixture was allowed to warm to room temperature and was stirred for 1 hr. The mixture was cooled to −25° C. and pivaloyl chloride (12 ml, 98 mmol) was added dropwise and allowed to stir for an additional 1 hr. THF (300 mL) was added followed by (S)-4-phenyloxazolidin-2-one (10 g, 61 mmol) and pivaloyl chloride (18 ml, 147 mmol) and the mixture was stirred at 100° C. for 1 hr and then room temperature for 18 hr. The reaction mixture was diluted with ethyl acetate (1 L) and washed with 5% NaHSO$_3$ (1 L). The resulting solid was collected by filtration and washed with water and diethyl ether to afford a light yellow solid (S,E)-3-(3-(1,4-dimethyl-1H-benzo[d][1,2,3]triazol-5-yl)acryloyl)-4-phenyloxazolidin-2-one (104.39 g, 288 mmol, 77% yield). $^1$H NMR (DMSO-d$_6$) δ: 8.05 (d, J=15.8 Hz, 1H), 7.71-7.88 (m, 3H), 7.30-7.45 (m, 5H), 5.61 (m, 1H), 4.83 (m, 1H), 4.30 (s, 3H), 4.24 (m, 1H), 2.78 (s, 3H). LC-MS: m/z 363.2 [M+H]$^+$ 1(o): (S)-3-((R)-3-(1,4-dimethyl-1H-benzo[d][1,2,3]triazol-5-yl)-3-(3-(((4-methoxybenzyl)oxy)methyl)-4-methylphenyl)propanoyl)-4-phenyloxazolidin-2-one

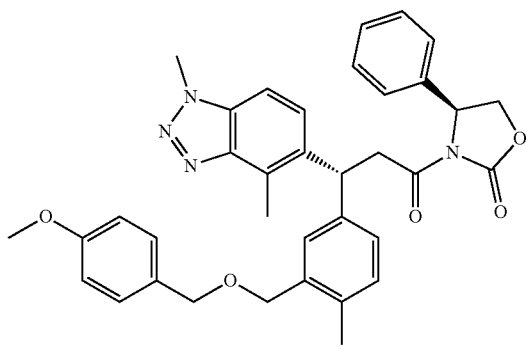 [SMILES: COc1ccc(COCc2cc([C@@H](CC(=O)N3C(=O)OC[C@@H]3c3ccccc3)c3ccc4c(nnn4C)c3C)ccc2C)cc1]

A mixture of magnesium (4.87 g, 200 mmol) and iodine (0.141 g, 0.556 mmol) was heated to 75° C. for 5 min. A solution of 4-bromo-2-(((4-methoxybenzyl)oxy)methyl)-1-methylbenzene (50.0 g, 156 mmol) in THF (200 mL) was added portionwise over 15 min and the mixture was stirred at reflux for 1 hr and then cooled to room temperature to give solution A. Separately, a mixture of copper(I) bromide-dimethyl sulfide complex (16.00 g, 78 mmol) in tetrahydrofuran (150 mL) was cooled to −40° C. and treated with dimethyl sulfide (41.1 mL, 556 mmol). The reaction mixture was stirred at −40° C. for 25 min. The cooled solution A was added dropwise over 1 hr maintaining a temperature between −35 & −45° C. The reaction mixture was allowed to warm to −20° C. and then (S,E)-3-(3-(1,4-dimethyl-1H-benzo[d][1,2,3]triazol-5-yl)acryloyl)-4-phenyloxazolidin-2-one (20.15 g, 55.6 mmol) was added in one portion. The resultant mixture was stirred at −20° C. for 30 min, then allowed to warm to −10° C. and was stirred for 30 minutes. Saturated aqueous ammonium chloride solution was added followed by ethyl acetate (1.5 L) and the layers were separated. The organic extract was washed with water (4×500 mL), brine, dried over sodium sulfate, filtered and the solvent evaporated to afford an oil which was purified by silica gel chromatography (0-100% ethyl acetate/hexane) to afford a white foam (S)-3-((R)-3-(1,4-dimethyl-1H-benzo[d][1,2,3]triazol-5-yl)-3-(3-(((4-methoxybenzyl)oxy)methyl)-4-methylphenyl)propanoyl)-4-phenyloxazolidin-2-one (24.5 g, 40.5 mmol, 73% yield). $^1$H NMR (DMSO-d$_6$) δ: 7.56 (m, 1H), 7.41 (d, m 1H), 7.21-7.25 (m, 3H), 7.16-7.20 (m, 3H), 7.04-7.16 (m, 4H), 6.82-6.89 (m, 2H), 5.36 (m, 1H), 4.91 (m, 1H), 4.69 (m, 1H), 4.34-4.41 (m, 4H), 4.24 (s, 3H), 4.10 (m, 1H), 3.88 (m, 1H), 3.74 (s, 3H), 3.60 (m, 1H), 2.70 (s, 3H), 2.18 (s, 3H). LC-MS: m/z 605.2 [M+H]$^+$

1(p): Ethyl (R)-3-(1,4-dimethyl-1H-benzo[d][1,2,3]triazol-5-yl)-3-(3-(((4-methoxybenzyl)oxy)methyl)-4-methylphenyl)propanoate

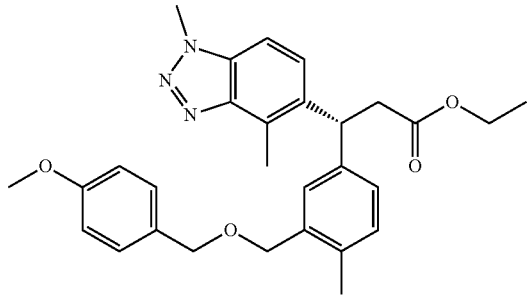 [SMILES: CCOC(=O)C[C@H](c1ccc(C)c(COCc2ccc(OC)cc2)c1)c1ccc2c(nnn2C)c1C]

To a solution of (S)-3-((R)-3-(1,4-dimethyl-1H-benzo[d][1,2,3]triazol-5-yl)-3-(3-(((4-methoxybenzyl)oxy)methyl)-4-methylphenyl)propanoyl)-4-phenyloxazolidin-2-one (2.140 g, 3.54 mmol) in ethanol (30 mL) was added magnesium bromide (1.629 g, 8.85 mmol) and the reaction mixture was stirred for 4 hr. Additional magnesium bromide (0.81 g, 4.5 mmol) was added and the mixture was stirred for 18 hr. Saturated aqueous ammonium chloride solution was added and the resultant white precipitate was collected and washed with ethanol to afford ethyl (R)-3-(1,4-dimethyl-1H-benzo[d][1,2,3]triazol-5-yl)-3-(3-(((4-methoxybenzyl)oxy)methyl)-4-methylphenyl)propanoate (1.46 g, 2.99 mmol, 85% yield). $^1$H NMR (DMSO-$d_6$) δ: 7.56-7.62 (m, 1H), 7.48 (m, 1H), 7.12-7.22 (m, 4H), 7.05-7.11 (m, 1H), 6.83-6.90 (m, 2H), 4.84 (m, 1H), 4.39 (m, 4H), 4.24 (s, 3H), 3.87-3.97 (m, 2H), 3.75 (s, 3H), 3.08-3.23 (m, 2H), 2.75 (s, 3H), 2.18 (s, 3H), 1.01 (m, 3H). LC-MS: m/z=488.2 [M+H]$^+$

1(q): Ethyl (R)-3-(1,4-dimethyl-1H-benzo[d][1,2,3]triazol-5-yl)-3-(3-(hydroxymethyl)-4-methylphenyl)propanoate

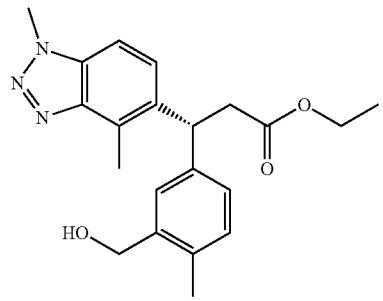 [SMILES: CCOC(=O)C[C@H](c1ccc(C)c(CO)c1)c1ccc2c(nnn2C)c1C]

To a solution of ethyl (R)-3-(1,4-dimethyl-1H-benzo[d][1,2,3]triazol-5-yl)-3-(3-(((4-methoxybenzyl)oxy)methyl)-4-methylphenyl)propanoate (53.6 g, 110 mmol), in dichloromethane (700 mL) was added water (35 mL) and the reaction mixture cooled to 0° C. DDQ (37.4 g, 165 mmol) was added and the reaction mixture was stirred at 0° C. for 2 hr. The reaction mixture was diluted with 10% sodium bicarbonate solution (1 L) and dichloromethane (750 ml) and was then filtered. The filtrate was separated and the aqueous layer extracted with dichloromethane (3×750 mL). The combined organic extracts were washed with water, brine, dried over sodium sulfate and concentrated under reduced pressure. The residue was purified by silica gel chromatography (0-100% ethyl acetate/hexanes) to afford an orange oil (R)-3-(1,4-dimethyl-1H-benzo[d][1,2,3]triazol-5-yl)-3-(3-(hydroxymethyl)-4-methylphenyl)propanoate (38.1 g, 104 mmol, 94%). $^1$H NMR (DMSO-$d_6$) δ: 7.55-7.63 (m, 1H), 7.46-7.52 (m, 1H), 7.26 (s, 1H), 7.07-7.14 (m, 1H), 6.99-7.06 (m, 1H), 4.98 (m, 1H), 4.85 (m, 1H), 4.41 (m, 2H), 4.25 (s, 3H), 3.94 (m, 2H), 3.07-3.21 (m, 2H), 2.76 (s, 3H), 2.16 (s, 3H), 1.03 (m, 3H). LC-MS: m/z=368.2 [M+H]$^+$

1(r): (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoate

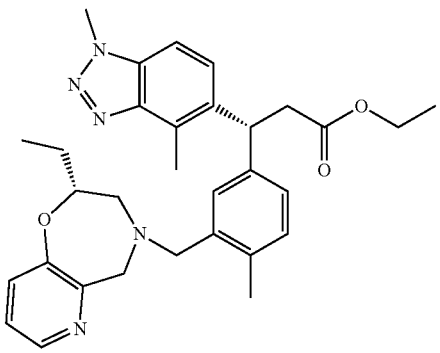 [SMILES: CCOC(=O)C[C@H](c1ccc(C)c(CN2Cc3ncccc3O[C@H](CC)C2)c1)c1ccc2c(nnn2C)c1C]

To a solution of ethyl (R)-3-(1,4-dimethyl-1H-benzo[d][1,2,3]triazol-5-yl)-3-(3-(hydroxymethyl)-4-methylphenyl)propanoate (10.10 g, 27.5 mmol) in chloroform (100 mL) was added thionyl chloride (4.01 mL, 55.0 mmol) and the reaction mixture was stirred for 1.5 hr at room temperature. The solvent was evaporated under reduced pressure and then azeotroped (3× chloroform). The residue was dissolved in acetonitrile (100 mL) and (R)-2-ethyl-2,3,4,5-tetrahydropyrido[2,3-f][1,4]oxazepine, hydrochloride (7.67 g, 35.7 mmol) and DIPEA (14.36 mL, 82 mmol) were added. The reaction mixture was heated to 60° C. for 18 hr. The reaction mixture was cooled, diluted with ethyl acetate, washed with water (2×), brine, dried over sodium sulfate, filtered and the solvent evaporated under reduced pressure. The crude residue was purified by silica gel chromatography (0-100% ethyl acetate/hexanes) to afford a white foam (R)-3-(1,4-dimethyl-1H-benzo[d][1,2,3]triazol-5-yl)-3-(3-(((R)-2-ethyl-2,3-dihydropyrido[2,3-t][1,4]oxazepin-4(5H)-yl)methyl)-4-methylphenyl)propanoate (13.76 g, 26.1 mmol, 95% yield). $^1$H NMR (DMSO-$d_6$) δ: 8.17 (m, 1H), 7.50-7.57 (m, 1H), 7.44-7.49 (m, 1H), 7.39 (m, 1H), 7.26 (m, 1H), 7.13 (s, 1H), 7.01-7.10 (m, 2H), 4.82 (m, 1H), 4.24 (s, 3H), 3.77-3.97 (m, 5H), 3.52 (s, 2H), 3.12 (m, 2H), 2.76-2.91 (m, 2H), 2.74 (s, 3H), 2.20 (s, 3H), 1.43-1.57 (m, 1H), 1.32 (m, 1H), 1.01 (m, 3H), 0.91 (m, 3H). LC-MS: m/z=528.4 [M+H]$^+$ 1(s): (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid

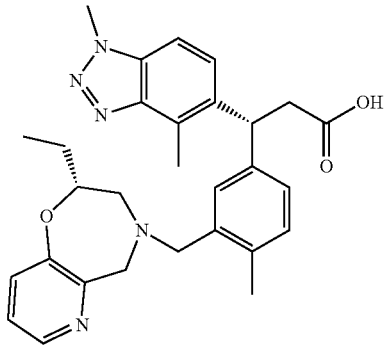 [SMILES: CC[C@@H]1CN(Cc2cc([C@@H](CC(=O)O)c3ccc4c(nnn4C)c3C)ccc2C)Cc2ncccc2O1]

To a solution of ethyl (R)-3-(1,4-dimethyl-1H-benzo[d][1,2,3]triazol-5-yl)-3-(3-(((R)-2-ethyl-2,3-dihydropyrido[2,3-t][1,4]oxazepin-4(5H)-yl)methyl)-4-methylphenyl)propanoate (23.00 g, 43.6 mmol) in methanol (350 mL) was added lithium hydroxide (10.44 g, 436 mmol) followed by water (350 mL) and the reaction mixture was stirred at 75° C. for 4 hr then cooled to room temperature and the solvents removed under reduced pressure. The residue was dissolved in water (500 mL) and the pH adjusted with 6N HCl and then 1N HCl to pH 5. The resultant precipitate was collected by filtration, washed with water and dried under vacuum to afford an off white solid. The solid was purified by silica gel chromatography (50-100% 3:1 EtOAc:EtOH/hexane) to afford a white foam, which was dried under vacuum to afford a cream solid (R)-3-(1,4-dimethyl-1H-benzo[d][1,2,3]triazol-5-yl)-3-(3-(((R)-2-ethyl-2,3-dihydropyrido[2,3-t][1,4]oxazepin-4(5H)-yl)methyl)-4-methylphenyl)propanoic acid (16.29 g, 32.5 mmol, 74.6% yield). $^1$H NMR (DMSO-d$_6$) δ: 12.14 (s, 1H), 8.17 (m, 1H), 7.50-7.56 (m, 1H), 7.44-7.49 (m, 1H), 7.40 (m, 1H), 7.27 (m, 1H), 7.00-7.15 (m, 3H), 4.80 (m, 1H), 4.23 (s, 3H), 3.77-3.98 (m, 3H), 3.52 (s, 2H), 2.93-3.11 (m, 2H), 2.69-2.92 (m, 5H), 2.20 (s, 3H), 1.48 (m, 1H), 1.29 (m, 1H), 0.90 (t, J=7.3 Hz, 3H). LC-MS: m/z 500.3 [M+H]$^+$ Example 2: (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoicacid, (−)-1-Deoxy-1-(methylamino)-D-glucitol salt

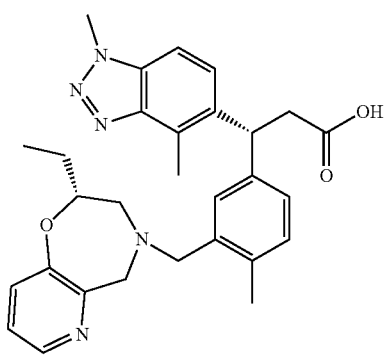 [SMILES: CC[C@@H]1CN(Cc2cc([C@@H](CC(=O)O)c3ccc4c(nnn4C)c3C)ccc2C)Cc2ncccc2O1]

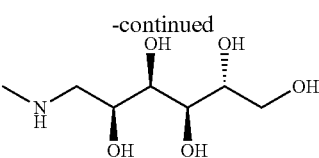

To a solution of (R)-3-(1,4-dimethyl-1H-benzo[d][1,2,3]triazol-5-yl)-3-(3-(((R)-2-ethyl-2,3-dihydropyrido[2,3-t][1,4]oxazepin-4(5H)-yl)methyl)-4-methylphenyl)propanoic acid (10.37 g, 20.76 mmol) dissolved in methyl isobutyl ketone (104 mL) was added a solution of (2R,3R,4R,5S)-6-(methylamino)hexane-1,2,3,4,5-pentaol (4.05 g, 20.76 mmol) in water (10.4 mL). The solvents were removed under reduced pressure and the residue was crystallized from ethanol (150 mL) to afford a white solid (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid, (−)-1-Deoxy-1-(methylamino)-D-glucitol salt (10.96 g, 15.62 mmol, 78% yield). LC-MS: m/z 500.3 [M+H]$^+$. $^1$H NMR (DMSO-d6) δ: 8.17 (m, 1H), 7.50 (m, 1H), 7.44 (m, 1H), 7.38 (m, 1H), 7.25 (m, 1H), 7.08 (s, 1H), 7.07-7.03 (m, 1H), 7.05-7.01 (m, 1H), 4.81 (m, 1H), 4.22 (s, 3H), 3.96-3.91 (m, 1H), 3.87-3.82 (m, 1H), 3.84-3.78 (m, 1H), 3.74-3.70 (m, 1H), 3.63 (m, 1H), 3.59 (m, 1H), 3.50 (s, 2H), 3.50-3.46 (m, 1H), 3.42-3.39 (m, 1H), 3.40-3.35 (m, 1H), 2.95-2.89 (m, 1H), 2.89-2.82 (m, 1H), 2.90-2.82 (m, 1H), 2.81-2.74 (m, 1H), 2.73 (s, 3H), 2.72-2.63 (m, 2H), 2.31 (s, 3H), 2.19 (s, 3H), 1.48 (m, 1H), 1.29 (m, 1H), 0.89 (m, 3H). Values used from CASS NMR report in DMSO. It will be understood that that no OH/NH are visible.

Crystallization:

The X-Ray Powder Diffraction Pattern (XRPD) was acquired on a PANalytical X'Pert Pro diffractometer using Ni-filtered Cu Kα (45 kV/40 mA) radiation and a step size of 0.02° 2θ and X'celerator TM RTMS (Real Time Multi-Strip) detector. Configuration on the incidental beam side: fixed divergence slit (0.25°), 0.04 rad Soller slits, anti-scatter slit (0.25°), and 10 mm beam mask. Configuration on the diffracted beam side: fixed divergence slit (0.25°) and 0.04 rad Soller slit. Samples were mounted flat on zero-background Si wafers. The X-ray powder diffraction (XRPD) pattern for the compound of Example 2 has the following representative peaks found in Table 2:

TABLE 2

| Pos. [°2Th.] | d-spacing [Å] |
| --- | --- |
| 3.452519 | 25.59182 |
| 6.870001 | 12.86693 |
| 9.778289 | 9.04557 |
| 10.79572 | 8.19525 |
| 12.14589 | 7.28712 |
| 12.72935 | 6.95439 |
| 13.63473 | 6.49457 |
| 15.19817 | 5.82981 |
| 16.04622 | 5.52356 |
| 17.25134 | 5.14032 |
| 17.51019 | 5.06491 |
| 18.058 | 4.91248 |
| 18.40831 | 4.81978 |
| 19.21405 | 4.61944 |
| 19.61405 | 4.52613 |
| 20.26727 | 4.3817 |
| 21.51128 | 4.13104 |
| 22.75124 | 3.90862 |
| 24.15621 | 3.68438 |
| 28.11324 | 3.17414 |

What is claimed is:
1. A compound which is (R)-3-(1,4-dimethyl-1H-benzo[d][1,2,3]triazol-5-yl)-3-(3-(((R)-2-ethyl-2,3-dihydropyrido[2,3-f][1,4]oxazepin-4(5H)-yl)methyl)-4-methylphenyl)propanoic acid:
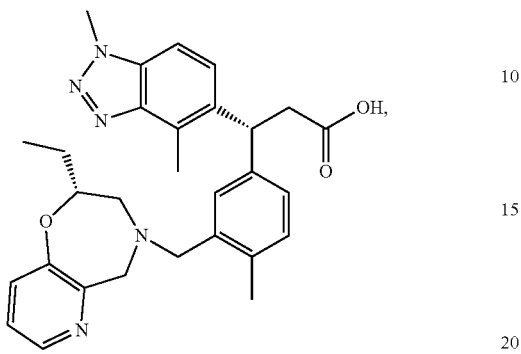
or a pharmaceutically acceptable salt thereof.
2. A pharmaceutical composition comprising the compound of claim 1 and one or more pharmaceutically acceptable excipients.
* * * * *